(12) United States Patent
Kurane et al.

(10) Patent No.: US 7,273,700 B2
(45) Date of Patent: Sep. 25, 2007

(54) NUCLEIC ACID PROBE AND NOVEL METHOD OF ASSAYING NUCLEIC ACID USING THE SAME

(75) Inventors: Ryuichiro Kurane, Tsukuba (JP); Takahiro Kanagawa, Tsukuba (JP); Yoichi Kamagata, Tsukuba (JP); Masaki Torimura, Tsukuba (JP); Shinya Kurata, Kurata (JP); Kazutaka Yamada, Tokyo (JP); Toyokazu Yokomaku, Yokomaku (JP)

(73) Assignees: National Institute of Advanced Industrial Science and Technology, Tokyo (JP); Kankyo Engineering Co., Ltd., Tokyo (JP)

( * ) Notice: Subject to any disclaimer, the term of this patent is extended or adjusted under 35 U.S.C. 154(b) by 322 days.

(21) Appl. No.: 10/399,407

(22) PCT Filed: Mar. 27, 2002

(86) PCT No.: PCT/JP02/03013

§ 371 (c)(1),
(2), (4) Date: Apr. 23, 2003

(87) PCT Pub. No.: WO02/077224

PCT Pub. Date: Oct. 3, 2002

(65) Prior Publication Data

US 2005/0048485 A1    Mar. 3, 2005

(30) Foreign Application Priority Data

Mar. 27, 2001  (JP)  .............................. 2001-090556

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | | |
|---|---|---|---|---|
| 5,952,202 A | * | 9/1999 | Aoyagi et al. | 435/91.2 |
| 6,492,121 B2 | * | 12/2002 | Kurane et al. | 435/6 |
| 6,495,326 B2 | * | 12/2002 | Kurane et al. | 435/6 |
| 6,699,661 B1 | * | 3/2004 | Kurane et al. | 435/6 |
| 7,081,336 B2 | * | 7/2006 | Bao et al. | 435/6 |
| 7,094,540 B2 | * | 8/2006 | Kurane et al. | 435/6 |
| 2001/0000148 A1 | * | 4/2001 | Kurane et al. | 435/6 |
| 2001/0000175 A1 | * | 4/2001 | Kurane et al. | 514/44 |
| 2002/0106653 A1 | * | 8/2002 | Kurane et al. | 435/6 |
| 2002/0150887 A1 | * | 10/2002 | Maruyama et al. | 435/5 |
| 2003/0082592 A1 | * | 5/2003 | Kurane et al. | 435/6 |
| 2004/0063137 A1 | * | 4/2004 | Kurane et al. | 435/6 |
| 2005/0048485 A1 | * | 3/2005 | Kurane et al. | 435/6 |
| 2006/0177856 A1 | * | 8/2006 | Kurane et al. | 435/6 |

FOREIGN PATENT DOCUMENTS

| | | |
|---|---|---|
| EP | 1046717 | 10/2000 |
| JP | 11-51935 | 2/1999 |
| JP | 2000-184894 | 7/2000 |
| JP | 2001-286300 | 10/2001 |

OTHER PUBLICATIONS

The Stratagene Catalog p. 39 (1988).*
S. Kurata et al.: "Fluorescent quenching-based quantitative detection of specific DNA/RNA using BODIPY FL-labeled probe or primer" Nucleic Acids Res., vol. 29, No. 6, p. e34, Mar. 15, 2001.
S. Tyagi et al.: "Wavelength-shifting molecular beacons" Nat. Biotechnol., vol. 18, pp. 1191-1196 2000.
M. Torimura et al.: "Fluorescent-quenching phenomenon by photoinduced electron transfer between a fluorescent dye and a nucleotide base" Anal. Sci., vol. 17, No. 1, pp. 155-160, 2000.
K.M. Parkhurst et al.: "Kinetic studies by fluorescence resonance energy transfer employing a double-labeled oligonucleotide: hybridization to the oligonucleotide complement and to single-stranded DNA" BIOCHEMISTRY, vol. 34, No. 1, pp. 285-292, 1995.
U.S. Appl. No. 09/556,127, filed Apr. 20, 2000, pending.
U.S. Appl. No. 09/725,265, filed Nov. 29, 2000, allowed.
U.S. Appl. No. 09/725,256, filed Nov. 29, 2000, allowed.
U.S. Appl. No. 10/209,608, filed Aug. 1, 2002, pending.
U.S. Appl. No. 09/891,517, filed Aug. 8, 2002, Kurane, et al.

* cited by examiner

*Primary Examiner*—Ethan Whisenant
(74) *Attorney, Agent, or Firm*—Oblon, Spivak, McClelland, Maier & Neustadt, P.C.

(57) ABSTRACT

A novel nucleic acid probe for nucleic acid determination includes a single-stranded nucleic acid labeled with plural fluorescent dyes containing at least one pair of fluorescent dyes to induce FRET, the pair of fluorescent dyes including a fluorescent dye (a donor dye) capable of serving as a donor dye and a fluorescent dye (an acceptor dye) capable of serving as an acceptor dye, in which the nucleic acid probe has such a base sequence and is labeled with the fluorescent dyes so that the fluorescence intensity of the acceptor dye decreases upon hybridization with a target nucleic acid. A novel nucleic acid determination method uses the probe. The probe and method can determine one or more types of target nucleic acids in an assay system in parallel using a simple apparatus.

26 Claims, No Drawings

NUCLEIC ACID PROBE AND NOVEL METHOD OF ASSAYING NUCLEIC ACID USING THE SAME

TECHNICAL FIELD

The present invention relates to, for example, a novel nucleic acid probe for determining one or more types of target nucleic acids (i.e., one or plural target nucleic acids) in an assay system and for determining such target nucleic acids, if plural, in an assay system in parallel using a simple apparatus and to a method for nucleic acid determination using the probe.

More specifically, it relates to a novel nucleic acid probe for nucleic acid determination, which comprises a single-stranded nucleic acid and is labeled with plural fluorescent dyes, which fluorescent dyes includes at least one pair of fluorescent dyes to induce fluorescence resonance energy transfer (hereinafter briefly referred to as "FRET"), which pair of fluorescent dyes includes a fluorescent dye capable of serving as a donor dye (hereinafter referred to as "donor dye") and a fluorescent dye capable of serving as an acceptor dye (hereinafter referred to as "acceptor dye"). It also relates to a method for nucleic acid determination using the nucleic acid probe, to a reagent kit for nucleic acid determination for use in the method, to a method for analyzing or determining polymorphism and/or mutation of target nucleic acids, and to an assay kit for use in the method just mentioned above.

BACKGROUND ART

Certain nucleic acid probes comprising a single-stranded oligonucleotide and a pair of fluorescent dyes to induce FRET including a donor dye fluorescein and an acceptor dye X-rhodamine are known in the art [Jikken Igaku (Experimental Medicine), 15, e7, 728-733 (1997)]. These nucleic acid probes are used in monitoring of polymerase chain reaction (PCR) and are not intended to direct determination of nucleic acids.

Some nucleic acid probes have been used for detecting a target nucleic acid (Biochemistry, 34, 285-292 (1995). In this case, the nucleic acid probe emits fluorescence at a low intensity, as a result of FRET, before hybridization with the target nucleic acid. Specifically, the fluorescein is prevented from emitting fluorescence and can emit fluorescence only at a low intensity. In contrast, the X-rhodamine is not so prevented from emitting fluorescence but emits fluorescence at an intensity lower than that of the prevented fluorescence emission of the fluorescein. Upon hybridization with the target nucleic acid, the probe changes in its conformation such that FRET disappears. As a result, the fluorescein emits fluorescence at an increasing intensity to thereby increase the fluorescence intensity of the whole reaction system. However, if a nucleic acid probe does not change in its conformation after hybridization, the fluorescence intensity does not change, and such a nucleic acid probe is not suitable for use in nucleic acid determination.

The present inventors have developed a nucleic acid probe, namely, "a fluorescence quenching nucleic acid probe" that decreases its fluorescence emission after hybridization with a target nucleic acid without the aid of another nucleic acid probe (Nucleic acid, 29, No. 6 e34 (2001); EP 1 046 717 A9; Japanese Patent Publication No. 2001-286300A). The nucleic acid probe comprises a single-stranded oligonucleotide labeled with a fluorescent dye in an end region. The fluorescent dye and the base sequence of the oligonucleotide are designed such that the fluorescence intensity decreases upon hybridization with the target nucleic acid. Use of the nucleic acid probe makes it possible to determine precisely, easily and in short time the target nucleic acid in a trace amount. However, this conventional method utilizes fluorescence quenching due to interaction between base-pair complex of G (guanine) and C (cytosine) combined through a hydrogen bond and the fluorescent dye upon the formation of a double-stranded oligonucleotide. In other words, the method utilizes fluorescence quenching due to emission energy transfer from the fluorescent dye to the complex. However, relatively a few type of fluorescent dye is subjected to quenching action according to this mechanism, and the method is limited in fluorescent colors that are usable.

When an assay system contains plural types of target nucleic acids, fluorescence colors of the number of color type(s) equal to that of the types of the target nucleic acids must be used to determine the target nucleic acids in parallel. In other words, nucleic acid probes emitting fluorescence of different colors in the number of type(s) equal to that of the types of the target nucleic acids are needed. In enlargement of the number of fluorescent color type(s) in the conventional method, the number of type(s) of fluorescent dyes are needed to be larger, which fluorescent dyes are capable of inducing interaction with the G-C hydrogen bonding pair and are different in emitting fluorescence colors. However, the types of fluorescent colors applicable to the conventional method are limited and thereby the method is limited in determining plural (specifically three or more) types of target nucleic acids in parallel. In addition, that types of fluorescent dyes are different in the conventional method means that exciting wavelengths different in types also are needed, thus requiring different types of excitation light sources to excite all the fluorescent dyes. The conventional method therefore requires an apparatus of a large-scale and is not economical.

Under these circumstances, it is an object of the present invention to provide a novel nucleic acid probe for nucleic acid determination ("novel nucleic acid probe for nucleic acid determination" may be hereinafter briefly referred to as "nucleic acid probe"), which includes a single-stranded oligonucleotide labeled with a pair of fluorescent dyes capable of inducing FRET and including a donor dye and an acceptor dye and can precisely and easily determine one or more types (i.e., one or plural types) of target nucleic acids in small amounts in parallel in a short time using a simple analyzer (instrument). Another object of the present invention is to provide a novel method for nucleic acid determination using the nucleic acid probe (hereinafter briefly referred to as "nucleic acid determination method"), a reagent kit for use in the method, a method for determining polymorphism and/or mutation of target nucleic acids, and an assay kit for use in the method just mentioned above.

DISCLOSURE OF INVENTION

Under consideration about the fluorescence quenching probe as a basic concept, the present inventors have made intensive investigations on different nucleic acid probes each including a single-stranded oligonucleotide labeled with different fluorescent dyes at two positions. As a result, they have obtained findings that, when the oligonucleotide is labeled at specific positions with a specific pair of a donor dye and an acceptor dye, the fluorescence intensity of the acceptor dye or the fluorescence intensities of both the donor dye and acceptor dye significantly decrease in a probe-nucleic acid complex (including the nucleic acid probe hybridized with the target nucleic acid) after hybridization with the target nucleic acid, which complex is formed by hybridization of the nucleic acid probe with the target nucleic acid. The present invention has been accomplished based on these findings.

Therefor, the present invention provides the following novel nucleic acid probes, methods, kits and devices:

1. A novel nucleic acid probe for determining one or more types of target nucleic acids in an assay system, comprising a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising a fluorescent dye (a donor dye) capable of serving as a donor dye and a fluorescent dye (an acceptor dye) capable of serving as an acceptor dye, wherein the nucleic acid probe has a base sequence and is labeled with the fluorescent dyes such that the fluorescence intensity of the acceptor dye decreases upon hybridization with a target nucleic acid.
2. The novel nucleic acid probe as described above under 1 for determining one or more target nucleic acids in an assay system, wherein the fluorescence intensities of the donor dye and acceptor dye decrease upon hybridization with the target nucleic acid.
3. The novel nucleic acid probe as described above under any one of 1 and 2 for determining one or more types of target nucleic acids in an assay system, wherein the fluorescent dye capable of serving as a donor dye is selected from BODIPY FL, BODIPY 493/503, 5-FAM, Tetramethylrhodamine, and 6-TAMRA.
4. The novel nucleic acid probe as described above under any one of 1 and 3 for determining one or more types of target nucleic acids in an assay system, which comprises one pair of the donor dye and the acceptor dye.
5. The novel nucleic acid probe as described above under any one of 1 and 4 for determining one or more types of target nucleic acids in an assay system, wherein the nucleic acid probe is labeled with the donor dye in an end region and has a base sequence designed such that, when the probe hybridizes with the target nucleic acid at the end region, the target nucleic acid has at least one G (guanine) in its base sequence as a first to third base from its terminal base hybridized with the probe.
6. The novel nucleic acid probe as described above under any one of 1 and 5 for determining one or more types of target nucleic acids in an assay system, wherein the nucleic acid probe has a base sequence designed such that that plural base pairs of a probe-nucleic acid hybrid in a region labeled with the donor dye constitute at least one pair of G (guanine) and C (cytosine) upon the hybridization with the target nucleic acid.
7. The novel nucleic acid probe as described above under any one of 1 and 6 for determining one or more types of target nucleic acids in an assay system, wherein the nucleic acid probe is labeled with the donor dye in a 5' end region inclusive of the 5' end.
8. The novel nucleic acid probe as described above under any one of 1 and 7 for determining one or more types of target nucleic acids in an assay system, wherein the nucleic acid probe is labeled with the donor dye in a 3' end region inclusive of the 3' end.
9. The novel nucleic acid probe as described above under 7 for determining one or more types of target nucleic acids in an assay system, wherein the nucleic acid probe has a G or C base at the 5' end and is labeled with the donor dye at the 5' end.
10. The novel nucleic acid probe as described above under 8 for determining one or more types of target nucleic acids in an assay system, wherein the nucleic acid probe has a G or C base at the 3' end and is labeled with the donor dye at the 3' end.
11. A novel method for nucleic acid determination, the method comprising the steps of adding one or more types of the nucleic acid probes according to any one of claims 1 to 10 into an assay system containing one or more types of target nucleic acids, the nucleic acid probe(s) being capable of hybridizing with the target nucleic acid(s), being in the number of type(s) equal to or larger than that of the target nucleic acid(s), and emitting fluorescence in different colors; allowing the nucleic acid probe(s) to hybridize to the target nucleic acid(s); and determining differential decrease(s) in fluorescence intensity between before and after hybridization at wavelength(s) in the number of type(s) equal to or larger than that of the types of the nucleic acid probe(s).
12. A kit for determining one or more types of target nucleic acids in an assay system, wherein said kit includes or accompanied by a nucleic acid probe as described above under any one of 1 to 10.
13. A method for analyzing or determining polymorphism and/or mutation of one or more types of target nucleic acids in an assay system, which comprises the steps of adding one or more types of the nucleic acid probes as described above under any one of 1 to 10 into an assay system containing one or more types of target nucleic acids, the nucleic acid probe(s) being capable of hybridizing with the target nucleic acid(s), being in the number of type(s) equal to or larger than that of the target nucleic acid(s), and emitting fluorescence in different colors; allowing the nucleic acid probe(s) to hybridize to the target nucleic acid(s); and determining differential decrease(s) in fluorescence intensity between before and after hybridization at wavelength(s) in the number of type(s) equal to or larger than that of the types of the nucleic acid probe(s).
14. A kit for analyzing or determining polymorphism and/or mutation of one or more types of target nucleic acids in an assay system, wherein said kit includes or accompanied by a nucleic acid probe as described above under any one of 1 to 10.
15. A method as described above under one of 11 and 13, wherein said target nucleic acids are one or more types of nucleic acids from cells of a microorganism obtained by single colony isolation or from cells of an animal.
16. A method as described above under one of 11 and 13, wherein said target nucleic acids are one or more types of nucleic acids contained in cells or a homogenate of cells, wherein cells are ones from a co-cultivation system of microorganisms or symbiotic cultivation system of microorganisms.

BEST MODE FOR CARRYING OUT THE INVENTION

The present invention will be described in further detail with reference to several preferred embodiments.

Specifically, the present invention provides, as a first invention, a nucleic acid probe for determining one or plural target nucleic acids, comprising a single-stranded oligonucleotide being labeled with plural fluorescent dyes, the plural fluorescent dyes containing at least one pair of fluorescent dyes to induce fluorescence resonance energy transfer (FRET), the pair of fluorescent dyes comprising a donor dye and an acceptor dye, in which the nucleic acid probe has a base sequence and is labeled with the fluorescent dyes such that the fluorescence intensity of the acceptor dye decreases in a probe-nucleic acid hybrid complex formed upon hybridization of the probe with a target nucleic acid. Among such nucleic acid probes, preferred probes are designed such that the fluorescence intensities of both the donor dye and acceptor dye decrease upon hybridization of the nucleic acids with the target nucleic acid.

The term "probe-nucleic acid hybrid complex" as used herein means one (complex) in which at least a nucleic acid probe according to the present invention, which is labeled with plural fluorescent dyes, and a target nucleic acid are hybridized with each other. For the same of brevity, it will hereinafter be called a "nucleic acid hybrid complex" in a shorten form.

The terms as used herein—such as nucleic acid probes, to hybridize, hybridization, stem-loop structures, quenching, quenching effects, DNAs, RNAs, cDNAs, mRNAs, rRNAs, XTPs, dXTPs, NTPs, dNTPs, nucleic acid probes, helper nucleic acid probes (or nucleic acid helper probes, or simply helper probes), to hybridize, hybridization, intercalators, primers, annealing, extending reactions, thermal denaturing reactions, nucleic acid melting curves, PCR, RT-PCR, RNA-primed PCR, stretch PCR, reverse PCR, PCR using Alu sequence(s), multiple PCR, PCR using mixed primers, PCR using PNA, hybridization assays, FISH methods (fluorescent in situ hybridization assays), PCR methods (polymerase chain assays), LCR methods (ligase chain reactions), SD methods (strand displacement assays), competitive hybridization, DNA chips, nucleic acid detecting (gene-detecting) devices, SNP (single nucleotide polymorphism), and co-cultivation systems of plural microorganisms—have the same meanings as the corresponding terms generally employed these days in molecular biology, genetic engineering, bioengineering and the like.

Further, the term "nucleic acid determination" as used herein means quantification, quantitative determination, qualitative detection, or mere detection of a target nucleic acid.

The term "target nucleic acid" as used herein means and includes any nucleic acid or gene the quantification, quantitative determination, qualitative detection, or mere detection of which is intended, irrespective whether it is in a purified form or not and further irrespective of its concentration. Nucleic acids other than the target nucleic acid may also coexist with the target nucleic acid. An assay system contains one or more types of target nucleic acids. The target nucleic acid may be, for example, at least one specific nucleic acid to be determined in a co-cultivation system of microorganisms (a mixed system containing RNAs or genetic DNAs of plural microorganisms) or in a symbiotic cultivation system of microorganisms (a mixed system containing RNAs or genetic DNAs of plural animals or plants and/or of plural microorganisms). The target nucleic acid can be purified, if needed, according to a conventionally known method. For example, it can be purified using a commercially available purification kit. Examples of the nucleic acids include DNAs, RNAs, PNAs, oligodeoxyribonucleotides, oligoribonucleotides, and chemically modified products of these nucleic acids. Such chemically modified nucleic acids include, for example, 2'-o-methyl(Me)-RNAs.

Donor dyes capable of serving as a donor dye in FRET for use in the present invention are specified as dyes satisfying at least the following conditions: (a) they are excited at a specific wavelength and emit light at a specific wavelength; (b) they can transfer their light-emitting energy to a specific dye (a dye capable of serving as an acceptor dye); and (c) when a G-C base pair complex (a G-C base pair complex bonded through hydrogen bonds; hereinafter briefly referred to as "G-C hydrogen bond complex" for sake of brevity in some parts of the description) is in the vicinity of the donor dye, they can transfer the energy to the base pair. Any dyes that satisfy these conditions can be used in the present invention. Among them, preferred dyes are those capable of serving as a donor dye in FRET, and when a nucleic acid probe labeled with the dye alone hybridizes with the target nucleic acid, the probe-nucleic acid hybrid complex emits fluorescence at a decreased intensity (Nucleic Acid, Vol. 29, Nol. 6, e34 (2001))

Illustrative of such donor dyes are BODIPY FL (trade names; products of Molecular Probes Inc., USA), BODIPY 493/503 (trade names; products of Molecular Probes Inc., USA), 5-FAM, Tetramethylrhodamine, 6-TAMRA, Fluorescein and derivatives thereof [for example, fluorescein isothiocyanate (FITC) and its derivatives]; Alexa 488, Alexa 532, cy3, cy5, EDANS (5-(2'-aminoethyl)amino-1-naphtalene sulfonic acid), rhodamine 6G (R6G) and its derivatives [for example, tetramethylrhodamine isothiocyanate (TM-RITC)], BODIPY FL/C3 (trade names; products of Molecular Probes Inc., USA), BODIPY FL/C6 (trade names; products of Molecular Probes Inc., USA), BODIPY 5-FAM(trade names; products of Molecular Probes Inc., USA),BODIPY TMR (trade names; products of Molecular Probes Inc., USA) or its derivatives [for example, BODIPY TR (trade names; products of Molecular Probes Inc., USA)], BODIPY R6G (trade names; products of Molecular Probes Inc., USA), BODIPY 564 (trade names; products of Molecular Probes Inc., USA),BODIPY 581/591 (trade names; products of Molecular Probes Inc., USA).

Among them, preferred donor dyes are BODIPY FL (trade name; a product of Molecular Probes Inc., USA), the BODIPY FL-series dyes (trade names; products of Molecular Probes Inc., USA), BODIPY 493/503 (trade name; a product of Molecular Probes Inc., USA), 5-FAM, BODIPY 5-FAM (trade name; a product of Molecular Probes Inc., USA), Tetramethylrhodamine, and 6-TAMRA, of which the BODIPY FL series dyes (trade name; a product of Molecular Probes Inc., USA), BODIPY 493/503 (trade name; a product of Molecular Probes Inc., USA), 5-FAM, Tetramethylrhodamine, and 6-TAMRA. The donor dyes for use in the present invention are, however, not limited to these examples.

Acceptor dyes for use in the present invention can be any dyes that are capable of serving as an acceptor dye in a pair with a donor dye, i.e., that are capable of receiving energy transferred from the donor dye. In other words, such acceptor dyes have quenching capability to the donor dye. The type of the acceptor dye depends on the type of the donor dye to constitute the pair. For example, X-rhodamine and BODIPY 581/591 (trade name; a product of Molecular Probes Inc., USA) can be used as the acceptor dye when the donor dye is any of the BODIPY FL series dyes (trade name; a product of Molecular Probes Inc., USA), BODIPY FL-series dyes (trade names; products of Molecular Probes Inc., USA), BODIPY 493/503 (trade name; a product of Molecular Probes Inc., USA), 5-FAM, BODIPY 5-FAM (trade name; a product of Molecular Probes Inc., USA), Tetramethylrhodamine, and 6-TAMRA. However, acceptor dyes for use in the present invention are not limited to these examples.

The nucleic acid probe according to the present invention, which is to be hybridized to the target nucleic acid, may be formed of either an oligodeoxyribonucleotide or an oligoribonucleotide. The nucleic acid probe may be a chimeric oligonucleotide which contains both of them. These oligonucleotides may be in chemically-modified forms. Such chemically-modified oligonucleotides may be inserted in chimeric oligonucleotides.

Examples of the modified positions of the chemically-modified oligonucleotide can include an end hydroxyl group or end phosphate group of an end portion of an oligonucleotide, the position of a phosphate portion of an internucleoside, the 5-carbon of a pyrimidine ring, and the position of a saccharide (ribose or deoxyribose) in a nucleoside. Preferred examples are the positions of ribose or deoxyribose. Specific examples can include 2'-O-alkyloligoribonucleotides ("2'-O-" will hereinafter be abbreviated as "2-O-"), 2-O-alkyleneoligo-ribonucleotides, and 2-O-benzyloligoribonucleotides. The oligonucleotide is modified at the OH group(s) on the 2'carbon(s) of one or more ribose molecules at desired positions thereof with alkyl group(s), alkylene group(s) or benzyl group(s) (via ether bond(s)). Preferred examples useful in the present invention can include, among 2-O-alkyloligo-ribonucleotides, 2-O-methyloligoribonucleotide, 2-O-ethyl-oligoribonucleotide and 2-O-butyloligoribonucleotide; among 2-O-alkyleneoligoribonucleotides, 2-O-ethyleneoligo-ribonucleotide; and 2-O-benzyloligoribonucleotide. Particularly preferably, 2-O-methyloligoribonucleotide (hereinafter simply abbreviated as "2-O-Me-oligo-ribonucleotide") can be used. Application of such chemical modification to an oligonucleotide enhances its affinity with a target nucleic acid so that the efficiency of hybridization with a nucleic acid probe according to the present invention is improved. The improved efficiency of hybridization leads to a further improvement in the rate of a decrease in the intensity of fluorescence from the fluorescent dye of the nucleic acid probe according to the present invention. As a consequence, the accuracy of determination of the concentration of the target nucleic acid is improved further.

Incidentally, it is to be noted that the term "oligonucleotide" as used herein means an oligodeoxy-ribonucleotide or an oligoribonucleotide or both of them and hence, is a generic term for them.

2-O-alkyloligoribonucleotides, 2-O-alkyleneoligo-ribonucleotides and 2-O-benzyloligoribonucleotide can be synthesized by a known process [Nucleic Acids Research, 26, 2224-2229 (1998)]. As custom DNA synthesis services are available from GENSET SA, France, they can be readily obtained. The present inventors have completed the present invention by conducting experiments with the compounds furnished by this company pursuant to our order.

Incidentally, use of a nucleic acid probe according to the present invention with modified DNA, such as 2-O-methyloligoribonucleotide (hereinafter simply called "2-O-Me-oligoribonucleotide), inserted in an oligodeoxy-ribonucleotide primarily for the determination of RNA, especially for the determination of rRNA can provide preferred results.

Upon determination of RNA by the nucleic acid probe according to the present invention, it is preferred to subject an RNA solution as a sample to heat treatment at 80 to 100° C., preferably 90 to 100° C., most preferably 93 to 97° C. for 1 to 15 minutes, preferably 2 to 10 minutes, most preferably 3 to 7 minutes before hybridization with the probe such that the higher-order structure of RNA can be degraded, as this heat treatment makes it possible to improve the efficiency of hybridization.

It is also preferred to add a helper probe to a hybridization reaction mixture for raising the efficiency of hybridization of the nucleic acid probe of this invention to the hybridization sequence region. In this case, the oligonucleotide of the helper probe can be an oligodeoxy-ribonucleotide, an oligorebionucleotide or an oligonucleotide subjected to similar chemical modification as described above. Examples of the above-described oligonucleotides can include those having the base sequence of (5')TCCTTTGAGT TCCCGGCCGG A(3') (SEQ ID NO: 1) as the forward type and those having the base sequence of (5')CCCTGGTCGT AAGGGCCATG ATGACTTGAC GT(3') (SEQ ID NO: 2) as the backward or the reverse type. Preferred examples of the chemically-modified oligonucleotide can include 2-O-alkyl-oligoribonucleotides, notably 2-O-Me-oligoribonucleotide.

Where the base strand of the nucleic acid probe according to the present invention is formed of 35 or fewer bases, use of a helper probe is particularly preferred. When a nucleic acid probe according to the present invention longer than a 35-base strand is used, however, it may only be necessary to thermally denature target RNA in some instances.

When the nucleic acid probe according to the present invention is hybridized to RNA as described above, the efficiency of hybridization is enhanced. The fluorescence intensity, therefore, decreases corresponding to the concentration of RNA in the reaction mixture so that RNA can be determined up to a final RNA concentration of about 150 pM.

The present invention also relates to an assay kit for determining the concentration of one or more (one or plural) of types of target nucleic acids in an assay system, which includes or carries one or more of the nucleic acid probes of the invention in the number of type(s) equal to or larger than the number of the target nucleic acid(s) and further includes or carries the helper probe.

In RNA determination according to a conventional hybridization method using a nucleic acid probe, an oligodeoxyribonucleotide or an oligoribonucleotide has been used as the nucleic acid probe. Because RNA itself has a higher-order firm structure, the efficiency of hybridization between the probe and the target RNA was poor, resulting quantification of low accuracy. The conventional methods therefore are accompanied by irksomeness that a hybridization reaction is conducted after denaturing RNA and immobilizing the denatured RNA on a membrane. In contrast, the method of the present invention uses a nucleic acid probe a ribose portion of which has been modified to have high affinity to a particular structural part of RNA, so that a hybridization reaction can be conducted a higher temperature as compared with the conventional methods. The adverse effect of the higher order structure of RNA can be avoided only by heat denaturation of the RNA as a pretreatment and the combination use of the helper probe. By this configuration, the method of the present invention can yield a hybridization efficiency of substantially 100% and can quantitatively determine the target RNA sufficiently. Further, the method according to the present invention is far significantly simplified as compared with the conventional method.

The probe of the present invention comprises 5 to 60 bases, preferably 10 to 35 bases, and typically preferably 15 to 20 bases. If the number of base(s) exceeds 60, the permeability of the nucleic acid probe through cell membranes of microorganisms may become lower when used in an FISH method, thereby narrowing the applicable ranges of the present invention. The number of base(s) smaller than 5 tends to induce non-specific hybridization, thus resulting in a large determination error.

The nucleic acid probe is labeled with the donor dye in an end region, and the base sequence thereof is designed so that the target nucleic acid has at least one C (cytosine) or G (guanine) in its base sequence as a first to third base from its terminal base upon hybridization of the probe in the end region with the target nucleic acid.

Preferably, the probe has a base sequence designed so that plural base pairs of the probe-nucleic acid hybrid in the region labeled with the donor dye form at least one pair between G (guanine) and C (cytosine) upon hybridization of the nucleic acid probe to the target nucleic acid.

More preferably, the probe is labeled with the donor dye at a G (guanine) or C (cytosine) base, at a phosphate group of a nucleotide having a G (guanine) or C (cytosine) base or at a OH group of the ribose moiety of the nucleotide.

When the nucleic acid probe is labeled with the donor dye at a base, phosphate moiety or ribose or deoxyribose moiety in a 5' end region, the nucleic acid probe may be labeled with the acceptor dye in its chain (strand) or in a 3' end region inclusive of the 3' terminal base. When the nucleic acid probe is labeled with the donor dye at a base, phosphate moiety or ribose moiety in a 3' end region, the nucleic acid probe may be labeled with the acceptor dye in its strand or in a 5' end region inclusive of the 5' terminal base. The end region can be labeled with the two dyes. For example, the nucleic acid probe may be labeled with one of the two dyes at the phosphate moiety and with the other at the ribose moiety or base moiety, when the base distance between bases labeled with the donor dye and those labeled with acceptor dye is zero as described later. Alternatively, the two dyes can be combined with one spacer having a side chain. It is also acceptable in the present invention that the nucleic acid probe is labeled with the donor dye and acceptor dye in its chain, as long as the resulting nucleic acid probe satisfies the above conditions.

The fluorescent dyes are preferably combined with the probe at a OH group or at an amino group with the interposition of a spacer.

The base distance between bases labeled with the donor dye and bases labeled with acceptor dye basically depends on the types of the pair of the donor dye and acceptor dye and is generally of from 0 to 50 bases, preferably of from 0 to 40 bases, more preferably of from 0 to 35 bases, and typically preferably of from 0 to 15 bases. If it exceeds of 50 bases, FRET becomes unstable. In some cases labeling at the distance of 15 to 50 bases, the donor dye exhibits an increased fluorescence intensity although the acceptor dye exhibits a decreased fluorescence intensity. In other words, the conformation of the nucleic acid probe changes upon hybridization with the target nucleic acid, thus inviting FRET between dyes of the nucleic acid probe to disappear in some cases. The fluorescence intensity of the donor dye increases or decreases after hybridization, which increasing or decreasing depends on the balance between quenching activity of the acceptor dye to the donor dye and the quenching activity of the G-C hydrogen bond complex to the donor dye. The fluorescence intensity decreases when the quenching activity of the G-C hydrogen bond complex is higher than that of the acceptor dye, and increases when the quenching activity of the G-C hydrogen bond complex is lower than that of the acceptor dye. If the distance is of less than 15 bases, both the fluorescence intensities of the donor dye and acceptor dye decrease after hybridization. In this case, the degree of decrease does not depend on the conformation of the nucleic acid probe after hybridization but only on the concentrations of the target nucleic acids in the assay system. To decrease both the fluorescence intensities of the donor dye and acceptor dye after hybridization, the distance is typically preferably of 0 to 10 bases.

A typically preferred embodiment of the probe of the present invention is a nucleic acid probe labeled with the donor dye and acceptor dye at the above specified distance, in which the donor dye is the BODIPY FL series dyes, BODIPY 493/503, 5-FAM, Tetramethylrhodamine, or 6-TAMRA, and the acceptor dye is BODIPY 581/591 or X-rhodamine, and the 5' terminal base is G or C and is labeled with the donor dye, or the 3' terminal base is G or C and is labeled with the donor dye.

The novel nucleic acid probe for nucleic acid determination of the present invention has the above-mentioned configuration. By this configuration, energy of the excited donor dye transfers to the acceptor dye before hybridization with a target nucleic acid. The acceptor dye thereby emits fluorescence with some intensity, and the donor dye is retarded from fluorescence emission and thus exhibits a low level of fluorescence intensity. When the nucleic acid probe hybridizes with the target nucleic acid, the energy of the donor dye transfers to the G-C hydrogen bond complex formed in the probe-nucleic acid hybrid complex. In addition, FRET disappears due to change in conformation of the nucleic acid probe in some cases. The fluorescent emission of the acceptor dye thus decreases.

The oligonucleotide moiety of the nucleic acid probe of the present invention can be prepared according to a conventional production process for praparing regular oligonucleotides. For example, it can be prepared by a chemical synthetic process or a production process using microorganisms and plasmid vectors or phage vectors (Tetrahedron letters 22, 1859-1862 (1981); and Nucleic Acids Research, 14, 6227-6245 (1986)). Commercially available nucleic acid synthesizers, such as ABI 394 (a product of PerkinElmer, Inc., USA), are preferably used.

To label the oligonucleotide with the fluorescent dyes, a desired one of conventionally known labeling method can be used (Nature Biotechnology, 14, 303-308 (1996); Applied and Environmental Microbiology, 63, 1143-1147 (1997); Nucleic Acids Research, 24, 4532-4535 (1996)). For example, the fluorescent dye molecule is combined with the oligonucleotide at the 5' end in the following manner. Initially, a spacer such as —$(CH_2)_n$—SH is introduced into the phosphate group at the 5' end according to conventional methods. Spacer-introduced products are commercially available and can be used herein (Midland Certified Reagent Company). In this case, n is from 3 to 8, and preferably 6. The oligonucleotide can be labeled by combining a fluorescent dye or its derivative having reactivity with SH group with the spacer. The prepared oligonucleotide labeled with the fluorescent dye can be purified by, for example, a reversed phase chromatographic method or the like and thereby yields a nucleic acid probe for use in the present invention.

The 3' terminal base of the oligonucleotide can also be labeled in the following manner.

In this labeling, a spacer, for example, —$(CH_2)_n$—$NH_2$ is introduced onto an OH group on the C carbon at the 3' position of the ribose or deoxyribose. Such spacer-introduced products are also commercially available and can be used herein (Midland Certified Reagent Company). In the above-mentioned example, n is from 3 to 8, and preferably from 4 to 7. By reacting an SH— or $NH_2$-reactive fluorescent dye to the linker or spacer, a labeled oligonucleotide can be prepared.

A base in the chain of the oligonucleotide can also be labeled.

In this labeling, the amino group or OH group of the base may be labeled with the dye according to the present invention in the same manner as in the 5' end or 3' end (ANALYTICAL BIOCHEMISTRY 225, 32-38 (1998)).

To introduce an amino group, kit reagents such as Unilink aminomodifier (a product of CLONTECH, USA), Fluo-Reporter Kit F-6082, F-6083, F-6084, and F-10220 (products of Molecular Probes Inc., USA) can be advantageously used. The fluorescent dye molecule can be jointed to the oligoribonucleotide according to a conventional method.

The labeled oligonucleotide as prepared as above is purified by, for example, a reversed phase chromatographic method and thereby yields the nucleic acid probe for use in the present invention.

The nucleic acid probe of the present invention can be prepared as described in the above manner. When the prepared nucleic acid probe for use in the nucleic acid determination of the present invention hybridizes with the target nucleic acid and forms a probe-nucleic acid hybrid complex, the complex emits fluorescence at a markedly decreased intensity as compared with that before the formation of the complex.

According to the present invention, one donor dye can be used in combination with plural types of acceptor dyes to thereby yield nucleic acid probes in the number of type(s) equal to that of the combinations. In addition, the nucleic acid probes have the above properties.

In actual nucleic acid determination, decrease in fluorescence intensity of the acceptor dye is measured. Accordingly, one or more types of nucleic acid probes can be used in parallel at one excitation wavelength. This means that, when one assay system includes one or more types of target nucleic acids, addition of such nucleic acid probes together to the assay system enables determination of the one or more types of target nucleic acids in parallel. Specifically, one or more types of nucleic acids can be determined in parallel using a simple apparatus.

A second invention of the present invention is a method for determining target nucleic acids using the above-prepared nucleic acid probes.

The method comprises the steps of adding one or more types of the nucleic acid probes, which probes are ones for use in the nucleic acid determination of the present invention, belonging to at least any one of the groups with the numerical symbols (the section nos.) 1 to 10 in the aforementioned description into an assay system containing one or more types of target nucleic acids, the nucleic acid probe(s) being capable of hybridizing with the target nucleic acid(s), being in the number of type(s) equal to or larger than that of types of the target nucleic acid(s), and emitting fluorescence in different colors; allowing the nucleic acid probe(s) to hybridize to the target nucleic acid(s); and determining differential decrease of fluorescence intensities between before and after hybridization at wavelengths in the number of type(s) equal to or larger than that of types of the nucleic acid probes. The present invention also relates to an assay kit therefor, a data analysis method for the determination, an device for the determination, and a computer-readable recording medium with various procedures of a data analysis method recorded as a program.

The term "assay system comprising one or more types of target nucleic acids" as used in the present invention means that the assay system contains one or plural types of target nucleic acids.

Further, the term "nucleic acid probe for use in the nucleic acid determination of the present invention belonging to at least any one of the groups with the numerical symbols (the section nos.) 1 to 10 in the afore mentioned description" means as follows.

When the assay system as used herein comprises one type of target nucleic acid, the type of the nucleic acid probes for nucleic acid determination to be added into the assay system may be singular or plural. The term "to may be plural" means that plural types of nucleic acid probes for use in the nucleic acid determination can be used with respect to the one type of target nucleic acid because the plural types of the nucleic acid probes can hybridize with plural specific sites having different base sequences.

When the assay system contains plural types of target nucleic acids, the present invention is characterized by the use of at least plural types of nucleic acid probes for use in the nucleic acid determination. The number of type(s) of the nucleic acids is at least equal to or larger than that of the types of the target nucleic acids. The term "to be at least equal to or larger than that of the types of the target nucleic acids" means that, in one type of target nucleic acid, plural types of base sequence sites may be set, which sites are capable of hybridizing independently with plural types of nucleic acid probes, and plural types of nucleic acid probes for use in the nucleic acid determination may be added with respect to one target nucleic acid into the assay system.

The term "plural types of nucleic acid probes for use in the nucleic acid determination probes" in the assay system containing one or plural types of target nucleic acids means as follows. (1) They are plural different types of probes among the nucleic acid probes for use in the nucleic acid determination according to any one of the groups with the numerical symbols (the section nos.) 1 to 10 in the above mentioned description. Illustrative such probes are plural probes having the same dimensions and structure but being labeled with different dyes. Alternatively, (2) they are plural types of the probes for use in the nucleic acid determination, having different dimensions or structures, being labeled with different dyes and being different in a combination of those. Namely, the probes may be plural types of probes belonging to different groups with the numerical symbols (the section nos.) 1 to 10 in the aforementioned description. An example of such a combination of probes is a combination of a probe belonging to the group with the numerical symbol (the section no.) 5, a probe belonging the group with the numerical symbol(the section no.) 6, and a probe belonging to the group with the numerical 10, each of which being labeled with a different dye from one another. However, this example illustration does not impose any limit on the scope of the present invention.

The terms in the following description have also the same meanings as defined above.

A third invention of the present invention is a method for analyzing or determining polymorphism and/or mutation of one or more types of target nucleic acids in an assay system, the method including the steps of adding one or more types of the nucleic acid probes belonging to at least one of the groups with the numerical symbols (the section nos.) 1 to 10 in the above mentioned description into an assay system containing one or more types of target nucleic acids, the nucleic acid probe(s) being capable of hybridizing with the target nucleic acid(s), being in the number of type(s) equal to or larger than that of the target nucleic acid(s), and being different in colors of emitting fluorescence; allowing the nucleic acid probe(s) to hybridize to the target nucleic acid(s); and determining differential decrease(s) in fluorescence intensity between before and after hybridization at wavelengths in the number of type(s) equal to or larger than that of the types of the nucleic acid probes. The invention also relates to an assay kit for the method, a data analysis method for the determination, a determination apparatus, and a computer-readable recording medium with various procedures of data analysis recorded as a program.

Namely, the nucleic acid probes of the present invention can be advantageously utilyzed not only for the nucleic acid determination but also for a method for analyzing or determining polymorphism and/or mutation of a target nucleic acid.

Specifically, the present invention provides a convenient method by using it in combination with the following DNA chip (Protein, Nucleic Acid and Enzyme, 43, 2004-2011 (1998)). The fluorescence intensity varies depending on whether a C-G pair is formed or not upon hybridization of the nucleic acid probe of the present invention. By allowing the nucleic acid probe of the present invention to hybridize to the target nucleic acid and determining the fluorescent intensity, polymorphism and/or mutation of the target nucleic acid can be analyzed or determined. Specific methods will be described in examples later. The target nucleic acid in these method may be an amplified product amplified according to desired one of various nucleic acid amplification methods or may be an extracted product. Further, the type of the target nucleic acid is not specifically limited, as long as it has a guanine base or cytosine base in its strand or at its end. If the target nucleic acid does not have a guanine base or cytosine base in its strand or at its end, the fluorescence intensity does not decrease. Accordingly, the method of the present invention can analyze or determine G→A, G←A, C→T, C←T, G→C, G←C mutations or substitutions, i.e.; single nucleotide polymorphisms (SNPs) and other polymorphisms. Such polymorphisms have been analyzed by sequencing the target nucleic acid using the Maxam-Gilbert method or dideoxy method.

The nucleic acid probe of the present invention was included in an assay kit for analyzing or determining polymorphism and mutation of a target nucleic acid, the resulting kit can be advantageously used as an assay kit for analyzing or determining polymorphism and/or mutation of the target nucleic acid.

On the analysis of data obtained by the method for analyzing or determining polymorphism and/or mutation of a target nucleic acid of the present invention, a processing step may be added to correct the fluorescence intensity, which is emitted from the reaction system when the target nucleic acid is hybridized with the nucleic acid probe of the present invention by the intensity of fluorescence emitted from the reaction system when the target nucleic acid and the nucleic acid probe are not hybridized with each other. The data so processed are provided with high reliability.

Accordingly, the present invention also provides a data analysis method for the method which analyzes or measures polymorphism and/or mutation of a target nucleic acid.

The present invention also features a system for analyzing or determining polymorphism and/or mutation of a target nucleic acid, which has processing means for correcting a fluorescence intensity of a reaction system, in which the target nucleic acid is hybridized with the nucleic acid probe according to the present invention, in accordance with a fluorescence intensity of the reaction system in which the target nucleic acid is not hybridized with the nucleic acid probe according to the present invention.

The present invention further features a computer-readable recording medium with procedures recorded as a program therein for making a computer perform a processing step in which, when analyzing data obtained by the method for analyzing or determining polymorphism and/or mutation of a target nucleic acid, a fluorescence intensity of a reaction system, in which the target nucleic acid is hybridized with the nucleic acid probe according to the present invention, is corrected in accordance with a fluorescence intensity of the reaction system in which the target nucleic acid or gene is not hybridized with the nucleic acid probe according to the present invention.

The third invention further provides a device for determining concentrations of plural nucleic acids, which comprises plural pieces of the nucleic acid probes for nucleic acid determination of the present invention combined with the surface of a substrate to allow target nucleic acids to hybridize with the probes to thereby determine the target nucleic acids. The device may constitute a device (a chip) for determining plural nucleic acids, which comprises the nucleic acid probes arranged and immobilized in an array on the surface of a solid substrate. The device may further comprise at least one each temperature sensor and heater per probe, which are disposed on a surface at an area of the solid substrate opposite to the nucleic acid probe. In this device, the temperatures of regions carrying the nucleic acid probes can be controlled to attain the optimum temperatures.

The nucleic acid probe according to the present invention may be immobilized on a surface of a solid (support layer), for example, on a surface of a slide glass. In this case, the probe may preferably be immobilized on the end not labeled with the fluorescent dye. The probe of this form is now called a "DNA chip". These DNA chips can be used for monitoring gene expressions, determining base sequences, analyzing mutations or analyzing polymorphisms such as single nucleotide polymorphism (SNP). Needless to say, they can also be used as devices (chips) for determining nucleic acids.

To bind the nucleic acid probe of the present invention, for example, to a surface of slide glass, the slide glass coated with polycations such as polylysine, polyethyleneimine and polyalkylamine, a slide glass carrying aldehyde groups introduced thereon or a slide glass carrying amino groups introduced thereon is initially prepared. Subsequently the nucleic acid probe can be immobilized to the slide glass in the following manner. i) Phosphate groups of the probe are allowed to react with the slide glass coated with polycations; ii) a probe carrying introduced amino groups is allowed to react with the slide glass carrying aldehyde groups; and iii) a probe carrying introduced pyridinium dichromate (PDC), amino groups or aldehyde groups is allowed to react with the slide glass carrying amino groups (Fodor, P. A., et al., Science, 251, 767-773, 1991; Schena, W., et al., Proc. Natl. Acad. Sci., U.S.A., 93, 10614-10619, 1996; McGal, G., et al., Proc. Natl. Acad. Sci., U.S.A., 93, 13555-13560, 1996; Blanchad, A. P., et al., Biosens. Bioelectron., 11, 687-690, 1996).

A device comprising the nucleic acid probes for nucleic acid determination of the present invention arranged and bound in an array on the surface of a solid support permits more convenient determination of the target nucleic acids.

One or more types of target nucleic acids can be determined in parallel by using a device comprising multiple types of the nucleic acid probes of the present invention having different base sequences arranged and bound on the surface of one solid support.

The device preferably further comprises at least one each temperature sensor and heater per probe, which are disposed on a surface opposite to the nucleic acid probes. In this device, the temperatures of regions carrying the nucleic acid probes can be controlled to thereby attain the optimum temperatures.

The determination method using the device of the present invention can be basically performed only by placing a solution containing a target nucleic acid on the surface of the solid support on which the nucleic acid probes are bound and then to thereby allow the probes to hybridize with the target nucleic acid. As a result, a change in the intensity of fluorescence takes place corresponding to the amount of the target nucleic acid, and the target nucleic acid can be then determined based on the changes in fluorescence. Further, binding multiple types of the nucleic acid probes of the present invention having different base sequences to the surface of a single support makes it possible to determine in parallel the concentrations of multiple types of target nucleic acids. The device is therefore a novel DNA chip, since it can be used in determination of target nucleic acids in the same use as in conventional DNA chips. Nucleic acids other than the target nucleic acids do not change the fluorescence emission under optimum reaction conditions, and the device does not require procedures for washing out unreacted nucleic acids. In addition, when the device comprises microheaters that can control the temperature per nucleic acid probe of the present invention to achieve the optimum reaction condition of each probe, the concentrations can be determined more precisely. The device can analyze dissociation curves between the nucleic acid probes of the present invention and the target nucleic acids by continuously changing the temperatures using the microheaters and determining the intensity of fluorescence during the changing of the temperature. It can also analyze the properties of the hybridized nucleic acids and/or detect SNPs based on differences in the dissociation curves.

In a conventional device for determining the concentration of a target nucleic acid, nucleic acid probes not modified with any fluorescent dye are bound or fixed to the surface of a solid support and subsequent to hybridization with the nucleic acid probes labeled with a fluorescent dye, an unhybridized target nucleic acids are washed out, followed by the measurement of intensity of fluorescence from the remaining fluorescent dye To label the target nucleic acid with the fluorescent dye, the following steps can be followed, for example, when specific mRNA is chosen as a target nucleic acid: (1) mRNAs is extracted in its entirety from cells; and (2) cDNAs is synthesized using a reverse transcriptase while inserting a nucleoside modified with a fluorescent dye. The present invention does not require these operations.

A number of various probes are applied in spots on the device. Optimum hybridization conditions, for example, temperatures or the like, for nucleic acids to be hybridized to the individual probes are different from each other. Theoretically speaking, it is therefore necessary to conduct a hybridization reaction and a washing operation under optimal conditions for each probe (at each spot). This is however physically impossible. For all the probes, hybridization is conducted at the same temperature and further, washing is also carried out at the same temperature with the same washing solution. The device is, therefore, accompanied by a drawback that a nucleic acid does not hybridize although its hybridization is desired or that, even if its hybridization takes place, the nucleic acid is readily washed off as the hybridization is not strong. For these reasons, the accuracy of quantification of the nucleic acid is low. The present invention does not have such a drawback because the above-mentioned washing operation is not needed. Further, a hybridization reaction can be conducted at an optimal temperature for each probe of the present invention by independently arranging a microheater at the bottom of each spot and controlling the hybridization temperature. Accordingly, the accuracy of quantification has been significantly improved in the present invention.

According to the present invention, one or more types of target nucleic acids in an assay system can be easily and specifically determined in a short time by using the nucleic acid probes or device for nucleic acid determination of the present invention. The determination method will be described below.

In the determination method of the present invention, the nucleic acid probes for nucleic acid determination of the present invention in the number of type(s) equal to or larger than that of target nucleic acids are added to the assay system to allow the probes to hybridize with the target nucleic acids according to a conventional or known procedure (Analytical Biochemistry, 183, 231-244 (1989); Nature Biotechnology, 14, 303-308 (1996); Applied and Environmental Microbiology, 63, 1143-1147 (1997)). For example, hybridization is performed at a salt concentration of 0 to 2 M and preferably 0.1 to 1.0 M, and at pH 6 to 8 and preferably pH 6.5 to 7.5.

The reaction temperature preferably falls within the range of Tm±10° C., where Tm is the melting temperature of a nucleic acid hybrid complex formed as a result of hybridization of the nucleic acid probe of the present invention with a specific site of the target nucleic acid. By setting the reaction temperature within this range, non-specific hybridization can be avoided. If the reaction temperature is lower than [Tm−10° C.], non-specific hybridization may occur, and if it exceeds [Tm+10° C.], hybridization may not occur. Tm can be determined in the same manner as in an experiment to design the nucleic acid probes of the present invention. Specifically, an oligonucleotide that is capable of hybridizing with the nucleic acid probe of the present invention and has a complementary base sequence to the nucleic acid probe is chemically synthesized using, for example, the nucleic acid synthesizer, and Tm of a nucleic acid hybrid complex with the nucleic acid probe is determined according to a conventional procedure. When the assay system contains plural target nucleic acids, the average of Tms of plural nucleic acid hybrid complexes or Tm of a target nucleic acid most valued can be used as Tm.

The reaction time is from 1 second to 180 minutes, and preferably from 5 seconds to 90 minutes. If the reaction time is less than 1 second, an increasing amount of the nucleic acid probes of the present invention may remain unreacted. In contrast, an excessively long reaction time is useless. The reaction time significantly depends on the types of the nucleic acids, i.e., the lengths or base sequences of nucleic acids.

Thus, the nucleic acid probes for nucleic acid determination of the present invention are allowed to hybridize with the target nucleic acids. Next, the fluorescence intensity of the hybridization reaction system before and after hybridization is measured at wavelengths in the number of type(s) equal to or larger than that of the types of the used nucleic acid determination probes using a fluorophotometer, and decrease at each wavelength is determined by calculation. The magnitudes of decrease are proportional to the concentrations of the target nucleic acids, and thereby the concentrations of the target nucleic acids can be determined based on the decrease.

The concentrations of the target nucleic acids in the reaction mixture are preferably from 0.1 to 10.0 nM. The concentrations of the nucleic acid probes of the present invention in the reaction mixture are preferably 1.0 to 25.0 nM. To plot a calibration curve, the ratio of the nucleic acid probe of the present invention to the target nucleic acid is preferably from 1.0 to 2.5.

Initially, a calibration curve is plotted under the above conditions to actually determine a target nucleic acid in an unknown concentration in a sample. When plural target nucleic acids are to be determined, calibration curves are plotted at individual measuring wavelengths of the nucleic acid probes of the present invention corresponding to the target nucleic acids. The nucleic acid probes of the present invention in plural concentrations are added to the sample, and decreases in fluorescence intensity of the individual nucleic acid probes are determined. In this procedure, a preferred probe concentration is defined as the concentration corresponding to the maximum decrease of the measured fluorescence intensities. A decrease in fluorescence intensity is determined using the probe in the preferred concentration, and the amount of the target nucleic acid is read from the decrease plotted in the calibration curve.

A fourth invention of the present invention is applied to nucleic acid determination processes such as fluorescence in situ hybridization (FISH), polymerase chain reactions (PCRs), ligase chain reactions (LCRs), SD process, competitive hybridization, and transcription-based amplification system (TAS).

Embodiments of the invention will be described below.

a) Application to FISH

The method of the present invention can be applied to nucleic acids contained in cells of microorganisms, plants or animals or those contained in homogenates of the respective cells. The method of the present invention can also be suitably applied to nucleic acids in cells of a cultivation system of microorganisms (e.g., a co-cultivation system of microorganisms or a symbiotic cultivation system of microorganisms), in which various kinds of microorganisms are contained together or a microorganism and other animal- or plant-derived cells are contained together and cannot be isolated from each other, or in a homogenate or the like of the cells of the cultivation system.

The term "microorganisms" as used herein means microorganisms in general sense, and no particular limitation is imposed thereon. Examples of such microorganisms can include eukaryotic microorganisms and prokaryotic microorganisms, and also mycoplasmas, virus and rickettsias. The term "a target nucleic acid" as used in connection with such a microorganism system means a nucleic acid with a base sequence specific to cells of a cell strain which is desired to be investigated, for example, as to how it is acting in the microorganism strain. Illustrative examples can include 5S rRNAs, 16S rRNAs and 23S rRNAs of certain specific cell strains and particular sequences of their gene DNAs.

According to the present invention, a nucleic acid probe is added to a co-cultivation system of microorganisms or a symbiotic cultivation system of microorganisms and the amount of 5S rRNA, 16S rRNA or 23S rRNA of a particular cell strain or its gene DNA, thereby making it possible to determine the viable count of the particular strain in the system. Incidentally, a viable count of a particular cell strain in a co-cultivation system of microorganisms or a symbiotic cultivation system of microorganisms can be determined by adding the nucleic acid probe to a homogenate of the system and then measuring the intensity of fluorescence emission from the fluorescent dye before and after hybridization. It is to be noted that this method also falls within the technical scope of the present invention.

The above-described determination method can be carried out as will be described hereinafter. Before the addition of the nucleic acid probe of the present invention, the temperature, salt concentration and pH of the co-cultivation system of microorganisms or the symbiotic cultivation system of microorganisms are adjusted to meet the conditions described above. It is also preferable to adjust the concentration of the specific cell strain, which is contained in the co-cultivation system of microorganisms or the symbiotic cultivation system of microorganisms, to $10^7$ to $10^{12}$ cells/mL, preferably $10^9$ to $10^{10}$ cells/mL in terms of viable count. These adjustments can be achieved by dilution, centrifugal or like concentration, or the like. A viable count smaller than $10^7$ cells/mL results in low fluorescence intensity and larger determination error. A viable count larger than $10^{12}$ cells/mL, on the other hand, leads to excessively high fluorescence intensity from the co-cultivation system of a microorganism or the symbiotic cultivation system of microorganisms, so that the viable count of the particular microorganism cannot be determined quantitatively. However, this range depends upon the performance of a fluorimeter to be used.

The concentration of the nucleic acid probe of the present invention to be added depends upon the viable count of the particular cell strain in the co-cultivation system of microorganisms or the symbiotic cultivation system of microorganisms and, at a viable count of $10^8$ cells/mL, may be in a range of from 0.1 to 10.0 nM, preferably in a range of from 0.5 to 5 nM, more preferably 1.0 nM. A probe concentration lower than 0.1 nM cannot provide any data which accurately reflects the viable count of the particular microorganism. The optimal concentration of the nucleic acid probe according to the present invention, however, cannot be specified in any wholesale manner because it depends upon the concentration of a target nucleic acid in cells.

Upon hybridizing the nucleic acid probe to the 5S rRNA, 16S rRNA or 23S rRNA of the particular cell strain or its gene DNA in the present invention, the reaction temperature may be set as described above. Further, the hybridization time may also be set as described above.

The nucleic acid probe according to the present invention is hybridized to the 5S rRNA, 16S rRNA or 23S rRNA of the particular cell strain or its gene DNA under such conditions as described above. Intensities of fluorescence from the fluorescent dye in the co-cultivation system of microorganisms or the symbiotic cultivation system of microorganisms before and after the hybridization are then measured.

The degree of the above determined increase in fluorescent intensity is proportional to the number of specified microorganism(s); its number is proportional to amounts of 5SrRNA, 16SrRNA, 23SrRNA or the genes of those contained in cells.

In the present invention, no particular limitation is imposed on components other than the microorganisms in the co-cultivation system of microorganisms or the symbiotic cultivation system of microorganisms, insofar as the components do not interfere with the hybridization between the nucleic acid probe according to the present invention and the 5S rRNA, 16S rRNA or 23S rRNA of the particular cell strain or its gene DNA and further, do not inhibit the emission of fluorescence from the fluorescent dye or the action of the quencher substance labeled on the oligonucleotide. For example, phosphates such as $KH_2PO_4$, $K_2HPO_4$, $NaH_2PO_4$ and $Na_2HPO_4$, inorganic nitrogens such as ammonium sulfate, ammonium nitrate and urea, various salts of ions such as magnesium, sodium, potassium and calcium, various salts such as the sulfates, hydrochlorides, carbonates and the like of trace metal ions such as manganese, zinc, iron and cobalt, and vitamins may be contained to adequate extent. If the above-described interference or inhibition is observed, it may be necessary to separate cells of the plural microorganisms from the cultivation system by an operation such as centrifugal separation and then to resuspend them in a buffer or the like.

Usable examples of the buffer can include various buffers such as phosphate buffer, carbonate buffer, Tris-HCl buffer, Tris-glycine buffer, citrate buffer, and Good's buffer. The buffer should be adjusted to a concentration not inhibiting the hybridization or the emission of fluorescence from the fluorescent dye. This concentration depends upon the kind of the buffer. The pH of the buffer may range from 4 to 12, with 5 to 9 being preferred.

b) Application to PCR Methods

The present invention can be applied to any method insofar as it is a PCR method. A description will hereinafter be made of an application of the present invention to a real-time quantitative PCR method.

In the real-time quantitative PCR method, PCR is conducted using a specific nucleic acid probe according to the present invention, and a decrease in fluorescent intensity of a reaction system after a reaction relative to fluorescent intensity of a reaction system before the reaction is determined in real time.

The term "PCR" as used herein means a variety of PCR methods. Examples can include RT-PCR, RNA-primed PCR, stretch PCR, reverse PCR, PCR making use of an Alu sequence, multiple PCR, PCR making use of a mixed primer, and PCR making use of PNA. Further, the term "quantitative" means, in addition to quantitation in general sense, quantitation of such an extent as detection as described above.

As described above, the term "target nucleic acid" as used herein means a nucleic acid the existing amount of which is intended to be determined, irrespective whether it is in a purified form or not and further irrespective of its concentration. Various other nucleic acids may also exist. For example, the target nucleic acid may be a specific nucleic acid in a co-cultivation system microorganisms (a mixed system of RNAs or gene DNAs of plural microorganisms) or a symbiotic cultivation system of microorganisms (a mixed system of RNAs or gene DNAs of plural animals, plants and/or microorganisms), the amplification of which is intended. Purification of the target nucleic acid, if needed, can be conducted by a method known per se in the art. For example, purification can be effected using a purification kit or the like available on the market.

The conventionally-known quantitative PCR methods individually amplify, in the presence of Mg ions, a target nucleic acid (DNA or RNA) by using DATP, dGTP, dCTP, dTTP or dUTP, the target nucleic acid, Taq polymerase, a primer, and a nucleic acid labeled with a fluorescent dye or an intercalator while repeatedly changing the temperature between low and high levels, and monitor increases in fluorescence emission from the fluorescent dye in real time in the course of the amplification [Jikken Igaku (Laboratory Medicine), 15(7), 46-51, Yodosha (1997)].

On the other hand, the quantitative PCR method according to the present invention is characterized in that one or more types of the target nucleic acids are amplified by using the nucleic probe of the present invention of the number of type(s) equal to or larger than that of the target nucleic acids and a change in fluorescent intensity in a reaction system is determined using wavelengths of the number of type(s) equal to or larger than that of the nucleic acid probes. The number of base(s) in a preferred probe of the present invention for use in the quantitative PCR according to the present invention may be from 5 to 50, preferably from 10 to 25, notably from 15 to 20. No particular limitation is imposed on the probe insofar as it hybridizes to amplification products of the target nucleic acid in PCR cycles. The probe may be designed in either a forward type or a reverse type.

Preferred nucleic acid probes for use herein are described below:

(1) Preferred nucleic acid probes are designed so that plural base pairs of the probe-nucleic acid hybrid at the region labeled with the donor dye constitute at least one G (guanine) and C (cytosine) pair upon or after hybridization with the target nucleic acids.

More preferably, (2) in the nucleic acid probes (1), more preferred are those labeled with the donor dye at a G (guanine) or C (cytosine) base, at a phosphate group of a nucleotide having a G or C base, or at a OH group of a ribose or deoxyribose and labeled with the acceptor dye in a 3' end region exclusive of the 3' end or in a chain.

(3) In the nucleic acid probes (2), more preferred are those labeled with the acceptor dye in a chain in the vicinity of a region labeled with the donor dye.

Specifically, among the nucleic acid probes of the present invention, a probe is utilized as a primer, which probe belongs to the above (1) and is labeled with a donor dye at a base of the 5' end domain or the base of the 5' end of a olygonucleotide of the nucleic acid probe and with an acceptor dye at the base in a strand(chain) of the olygonucleotide or at the base of its 3' end.

When the nucleic acid probe of the present invention is used as a primer and cannot be designed to have G or C at the 3' end or 5' end due to the base sequence of the target nucleic acid, the objects of the present invention can also be achieved by adding 5'-guanylic acid or guanosine, or 5'-cytidylic acid or cytidine to the 5' end of an oligonucleotide as a primer designed based on the base sequence of the target nucleic acid. The objects of the present invention can also be advantageously achieved by adding 5'-guanylic acid or 5'-cytidylic acid to the 3' end. The term "nucleic acid probes designed so that to have G or C at 3' end or 5' end" used herein means and includes probes designed based on the base sequences of target nucleic acids, as well as those prepared by adding 5'-guanylic acid or guanosine or 5'-cytidylic acid or cytidine to the 5' end of the designed probes and those prepared by adding 5'-guanylic acid or 5'-cytidylic acid to the 3' end of the designed probes.

In particular, when a nucleic acid probe among the above-described probe (2) of the present invention is labeled with a donor dye at a base of the 3' end domain (including the base of the 3' end) or ribose or deoxyribose of the 3' end, such a probe and with an acceptor dye at a base in the strand is designed to be not used as a primer. The method using such a single probe of the present invention can be utilized as one substituting for a conventional method using two (fluorescent-dye-labeled) probes that have been up to the present used in a real-time quantitative PCR method utilizing the FRET phenomenon. The probe is added to a PCR reaction system, and PCR is then conducted. During a nucleic acid extending reaction, the probe which has been in a form hybridized with the target nucleic acid or amplified target nucleic acid is degraded by polymerase and is dissociated off from the nucleic acid. hybrid complex. The intensity of fluorescence of the reaction system at this time or the reaction system in which a nucleic acid denaturing reaction has completed is measured. Further, the intensity of fluorescence of the reaction system in which the target nucleic acid or amplified target nucleic acid has hybridized with the probe (i.e., the reaction system at the time of an annealing reaction or at the time of the nucleic acid extending reaction until the probe is eliminated from the nucleic acid hybrid complex by polymerase). By calculating the rate of a decrease of the latter fluorescence intensity from the former fluorescence intensity, the amplified nucleic acid is determined. The intensity of fluorescence is high when the probe has completely dissociated from the target nucleic acid or amplified target nucleic acid by the nucleic acid denaturing reaction or when the probe has been degraded out from the hybrid complex of the probe and the target nucleic acid or amplified nucleic acid at the time of extension of the nucleic acid. However, the intensity of fluorescence of the reaction system in which an annealing reaction has been completed and the probe has fully hybridized to the target nucleic acid or amplified target nucleic acid or of the reaction system until the probe is degraded out of the hybrid complex of the probe and the target nucleic acid or amplified target nucleic acid by polymerase at the time of a nucleic acid extending reaction is lower than the former. The decrease in the intensity of fluorescence is proportional to the concentration of the amplified nucleic acid.

In this case, the base sequence of the probe (2) may desirably be designed such that the Tm of a nucleic acid hybrid complex, which is available upon hybridization of the probe with the target nucleic acid, falls within a range of the Tm value of the nucleic acid hybrid complex as a primer ±15° C., preferably ±5° C. If the Tm of the probe is lower than (the Tm value of the primer −5° C.), especially (the Tm value of the primer −15° C.), the probe does not hybridize so that no decrease takes place in the fluorescence emission from the fluorescent dye. If the Tm of the probe is higher than (the Tm value of the primer +5° C.), especially (the Tm value of the primer +15° C.), on the other hand, the probe also hybridizes to nucleic acid or acids other than the target nucleic acid so that the specificity of the probe is lost.

The probes other than the probe (2), especially the probe (1) is added as a primer to PCR reaction systems. Except for the PCR method according to the present invention, no PCR method is known to make use of a primer labeled with a fluorescent dye. As the PCR reaction proceeds, the amplified nucleic acid is progressively labeled with the fluorescent dye useful in the practice of the present invention. Accordingly, the intensity of fluorescence of the reaction system in which the nucleic acid denaturing reaction has completed is high but, in the reaction system in which the annealing reaction has completed or the nucleic acid extending reaction is proceeding, the intensity of fluorescence of the reaction system is lower than the former intensity of fluorescence.

The PCR reaction can be conducted under similar conditions as in conventional PCR methods. It is, therefore, possible to conduct amplification of a target nucleic acid in a reaction system the concentration of Mg ions in which is low (1 to 2 mM). Needless to say, the present invention can also be conducted even in a reaction system in which Mg ions are contained at such a high concentration (2 to 4 mM) as that employed in the conventionally-known quantitative PCR methods.

Incidentally, in the PCR method according to the present invention, Tm value can be determined by conducting the PCR of the present invention and then analyzing the melting curve of the nucleic acids with respect to the amplification products by using the number of type(s) of wavelengths equal to that of types of the used nucleic acid probes. This method is a novel analysis method of a melting curve of a nucleic acid. In this method, the nucleic acid probe employed as a nucleic acid probe or primer in the PCR method of the present invention can be used suitably.

In this case, designing of the base sequence of the nucleic acid probe according to the present invention into a sequence complementary with a region containing SNP (single nucleotide polymorphism) makes it possible to detect SNP from a difference, if any, in a dissociation curve of the nucleic acid from the nucleic acid probe of the present invention by analyzing the dissociation curve after completion of PCR. If a base sequence complementary with an SNP-containing sequence is used as a sequence for the nucleic acid probe of the present invention, a Tm value available from a dissociation curve between the sequence of the probe and the SNP-containing sequence becomes higher than a Tm value available from a dissociation curve between the sequence of the probe and the SNP-free sequence.

The fifth invention of the present invention relates to the method for analyzing data obtained by the above-described real-time quantitative PCR method.

A real-time quantitative PCR method is now practiced in real time by a system which is composed of a reactor for conducting PCR, equipment for detecting fluorescence emission from a fluorescent dye, a user interface, namely, a computer-readable recording medium with various procedures of a data analysis method recorded as a program (also called "sequence detection software system"), and a computer for controlling them and analyzing data. Determination by the present invention is also conducted by such a system.

A description will first be made of an analyzer for real-time quantitative PCR. Any system can be used in the present invention insofar as it can monitor PCR in real time. Particularly suitable examples can include "ABI PRISM™ 7700 Sequence Detection System SDS 7700" (manufactured by PerkinElmer Applied Biosystems, Inc., U.S.A.) and "LightCycler™ System" (manufactured by Roche Diagnostics, Germany).

The above-described PCR reactor is an apparatus for repeatedly conducting a thermal denaturing reaction of a target nucleic acid, an annealing reaction and an extending reaction of the nucleic acid (these reactions can be repeatedly conducted, for example, by successively changing the temperature to 95° C., 60° C. and 72° C.). The detection system comprises a fluorescence emitting argon laser, a spectrograph and a CCD camera. Further, the computer-readable recording medium with the various procedures of the data analysis method recorded as the program is used by installing it in the computer, and contains a program recorded therein for controlling the above-described system via the computer and also for processing and analyzing data outputted from the detection system.

The data analysis program recorded in the computer-readable recording medium comprises the following steps: measuring the intensity of fluorescence cycle by cycle, displaying each measured fluorescence intensity as a function of cycles, namely, as a PCR amplification plot on a display of the computer, calculating a threshold cycle number (Ct) at which the intensity of fluorescence is begun to be detected, forming a working line useful in determining from Ct values the number of copy(ies) of the nucleic acid in the sample, and printing data and plot values in the respective steps. When PCR is exponentially proceeding, a linear relationship is established between the logarithm of the number of copy(ies) of the target nucleic acid at the time of initiation of PCR and Ct. It is therefore possible to calculate the number of copy(ies) of the target nucleic acid at the time of initiation of PCR by forming a working line based on known copy numbers of the target nucleic acid and detecting the Ct of a sample which contains the target nucleic acid the number of copy(ies) of which is unknown.

c) A Method for Analyzing Data Obtained by the above PCR Method, an Apparatus for Analyzing the Data and a Computer-readable Recording Medium with Various Procedures Making the Computer Conduct the Method.

The PCR-related invention such as the above-described data analysis method is a method for analyzing data obtained by such a real-time quantitative PCR method as described above. Its respective features will be described hereinafter.

A first feature resides in a processing step for correcting a fluorescence intensity of a reaction system, which is measured when the amplified nucleic acid hybridizes to a nucleic acid probe according to the present invention in the method for analyzing data obtained by the real-time quantitative PCR method, by a fluorescence intensity of the reaction system as obtained when the above-described hybrid complex of the nucleic acid probe of the present invention and the target nucleic acid or the nucleic acid hybrid complex has dissociated in each cycle, namely, the first feature resides in a correction-processing step.

As a specific example of "the reaction system . . . when the amplified target nucleic acid hybridizes to a nucleic acid probe according to the present invention", a reaction system upon conducting a nucleic acid extending reaction or annealing at 40 to 85° C., preferably 50 to 80° C. in each cycle of PCR can be mentioned. It also means a reaction system in which such a reaction has been completed. The actual temperature depends upon the length of the amplified nucleic acid.

Further, "the reaction system . . . when the above-described nucleic acid hybrid complex has dissociated" can be a reaction system upon conducting thermal denaturation of the nucleic acid in each cycle of PCR, specifically at a reaction temperature of from 90 to 100° C., preferably 94 to 96° C. Illustrative is a system in which the reaction has been completed.

Any correction processing can be used as the correction processing in the correction processing step insofar as it conforms with the objects of the present invention. Specifically, correction processing including a processing step by the following formula (1) or formula (2) can be exemplified.

$$f_n = f_{hyb,n} / f_{den,n} \quad (1)$$

$$f_n = f_{den,n} / f_{hyb,n} \quad (2)$$

where
- $f_n$: correction-processed value in an $n^{th}$ cycle as calculated in accordance with the formula (1) or formula (2),
- $f_{hyb,n}$: intensity value of fluorescence of the reaction system available after the amplified nucleic acid has hybridized to the nucleic acid probe labeled with the fluorescent dye in the $n^{th}$ cycle, and
- $f_{den,n}$: intensity value of fluorescence of the reaction system available after the nucleic acid hybrid complex has dissociated in the $n^{th}$ cycle.

This step includes a sub-step in which correction-processed values obtained by the above-described processing are displayed on a computer display and/or the correction-processed values are likewise displayed and/or printed in the form of a graph as a function of cycles.

A second feature resides in a data analysis method, which comprises introducing correction-processed values, which have been calculated in accordance with the formula (1) or formula (2) in individual cycles, into the following formula (3) or formula (4) to calculate rates or percentages of changes in fluorescence between samples in the individual cycles:

$$F_n = f_n / f_a \quad (3)$$

$$F_n = f_a / f_n \quad (4)$$

where
- $F_n$: rate or percentage of a change in fluorescence in an $n^{th}$ cycle as calculated in accordance with the formula (3) or formula (4),
- $f_n$: correction-processed value calculated in the $n^{th}$ cycle as calculated in accordance with the formula (1) or formula (2), and
- $f_a$: correction-processed value calculated in a given cycle before a change in $f_n$ is observed as calculated in accordance with the formula (1) or formula (2), and in general, a correction-processed value, for example, in one of $10^{th}$ to $40^{th}$ cycles, preferably one of $15^{th}$ to $30^{th}$ cycles, more preferably one of $20^{th}$ to $30^{th}$ cycles is adopted; and comparing the rates or percentages of changes in fluorescence.

This step includes a sub-step in which calculated values obtained by the above-described processing are displayed on a computer display and/or are printed or comparative values or the calculated values are likewise displayed and/or printed in the form of a graph as a function of cycles. This sub-step may be applied or may not be applied to the correction-processed values obtained by the formula (1) or formula (2).

A third feature resides in a data analysis method, which comprises the following processing steps:

3.1) performing processing in accordance with the following formula (5), (6) or (7) by using data of rates or percentages of changes in fluorescence as calculated in accordance with said formula (3) or (4):

$$\log_b (F_n), \ln(F_n) \quad (5)$$

$$\log_b \{(1-F_n) \times A\}, \ln \{(1-F_n) \times A\} \quad (6)$$

$$\log_b \{(F_n-1) \times A\}, \ln \{(F_n-1) \times A\} \quad (7)$$

where
- A,b: desired numerical values, preferably integers, more preferably natural numbers and, when A=100, b=10, $\{(F_n-1) \times A\}$ is expressed in terms of percentage (%), and
- $F_n$: rate or percentage of a change in fluorescence in an $n^{th}$ cycle as calculated in accordance with the formula (3) or formula (4), 3.2) determining a cycle in which said processed value of said processing step 3.1) has reached a constant value, 3.3) calculating a relational expression between cycle of a nucleic acid sample of a known concentration and the number of copy(ies) of said target nucleic acid at the time of initiation of a reaction, and 3.4) determining the number of copy(ies) of said target nucleic acid in an unknown sample upon initiation of PCR.

Preferably, these steps are performed in the order of 3.1)→3.2)→3.3)→3.4).

Each of these steps 3.1) to 3.3) may include a sub-step in which processed values obtained by the corresponding processing are displayed on a computer display and/or the processed values are likewise displayed and/or printed in the form of a graph as a function of cycles. The step 3.4) should include at least a printing sub-step as the processed values obtained in the step 3.4) have to be printed, although the processed values obtained in the step 3.4) may also displayed on a computer display.

Incidentally, the correction-processed values obtained by the formula (1) or (2) and the calculated values obtained by the formula (3) or (4) may be or may not be displayed on a computer display and/or printed in the form of graphs as a function of cycles, respectively. These displaying and/or printing sub-steps may, therefore, be added as needed.

A fourth feature resides in an analysis system for real-time quantitative PCR, which comprises processing and storing means for performing a data analysis method for the above-described real-time quantitative PCR method of the present invention.

A fifth feature resides in a computer-readable recording medium with individual procedures of a data analysis method, which is adapted to analyze PCR by using the analysis system for the real-time quantitative PCR, stored as a program therein, wherein the program is designed to make a computer perform the individual procedures of the data analysis method of the present invention.

A sixth feature resides in a novel method for determining a nucleic acid, which comprises using the data analysis method, determination and/or analysis system and/or recording medium of the present invention in the nucleic acid determination method.

Specifically, the sixth feature resides in an analysis method, which comprises the following steps: gradually heating a nucleic acid, which has been amplified by the PCR method of the present invention, from a low temperature until complete denaturation of the nucleic acid (for example, from 50° C. to 95° C.); measuring an intensity of fluorescence at short time intervals (for example, at intervals equivalent to a temperature rise of from 0.2° C. to 0.5° C.) during the heating step; displaying results of the measurement as a function of time on a display, namely, a melting curve of the nucleic acid; differentiating the melting curve to obtain differentiated values (−dF/dT, F: intensity of fluorescence, T: time); displaying the differentiated values as derivatives on the display; and determining a point of inflection from the derivatives. In the present invention, the intensity of fluorescence increases as the temperature rises. Preferable results can be obtained in the present invention by adding to the above-described step a further processing step in which in each cycle, the intensity of fluorescence at the time of the nucleic acid extending reaction, preferably at the time of completion of the PCR reaction is divided by the value of fluorescence intensity at the time of the thermal denaturing reaction.

A measurement and/or analysis system for the real-time quantitative PCR of the present invention, said real-time quantitative PCR including the method of the present invention for the analysis of the melting curve of a nucleic acid added to the above-described novel method of the present invention for the analysis of data obtained by a PCR method, also falls within the technical scope of the present invention.

Further, a seventh feature resides in a computer-readable recording medium with the individual procedures of the method of the present invention for the analysis of the melting curve of a nucleic acid recorded therein as a program such that the procedures can be performed by a computer or a computer-readable recording medium with the individual procedures of the method of the present invention for the analysis of data obtained by a PCR method recorded therein as a program such that the procedures can be performed by a computer, wherein a program designed to make the computer perform the individual procedures of the method of the present invention for the analysis of the melting curve of the nucleic acid is additionally recorded.

The above-described data analysis methods, systems and recording media of the present invention can be used in a variety of fields such as medicine, forensic medicine, anthropology, paleontology, biology, genetic engineering, molecular biology, agricultural science and phytobreeding. They can be suitably applied to microorganism systems called "co-cultivation systems of microorganisms" or "symbiotic cultivation systems of microorganisms", in each of which various kinds of microorganisms are contained together or a microorganism and other animal- or plant-derived cells are contained together and cannot be isolated from each other. The term "microorganisms" as used herein means microorganisms in general sense, and no particular limitation shall be imposed thereon. Illustrative are eukaryotic microorganisms, prokaryotic microorganisms, mycoplasmas, viruses and rickettsias.

The vial count of a particular cell strain in a co-cultivation system of microorganisms or a symbiotic cultivation systems of microorganisms can be determined by determining the number of copy(ies) of the 5S rRNA, 16S rRNA or 23S rRNA of the particular cell strain or its gene DNA in the system by using one or more of the above-described data analysis methods, systems and recording media of the present invention, because the number of copy(ies) of the gene DNA of 5S rRNA, 16S rRNA or 23S rRNA is specific to each cell strain. In the present invention, the vial count of a particular cell strain can also be determined by applying the real-time quantitative PCR of the present invention to a homogenate of a co-cultivation system of microorganisms or a symbiotic cultivation systems of microorganisms. It shall also be noted that this method also falls with the technical scope of the present invention.

EXAMPLES

The present invention will be illustrated in further detail with reference to several examples and comparative examples below.

Example 1

Preparation of Nucleic Acid Probe:

Assuming that a target nucleic acid A comprises an oligodeoxyribonucleotide having a base sequence of (5')tgc cat ccc ctc ant gg(3') (SEQ ID NO: 3), a nucleic acid probe according to the present invention was prepared in the following manner.

Designing of Nucleic Acid Probe:

Based on the base sequence of the target nucleic acid, the nucleic acid probe could be easily designed as an oligodeoxyribonucleotide having a base sequence of (5')cca ttg agg gga tgg ca(3') (SEQ ID NO: 4). The nucleic acid probe of the present invention was designed in the following manner. The nucleic acid probe was to be labeled with a donor dye BODIPY FL (Molecular Probes Inc., USA) at a phosphate group at the 5' end and to be labeled with an acceptor dye BODIPY 581/591 (Molecular Probes Inc., D-2228, USA) at a OH group on the carbon atom at the 6-position of the base ring of thymine, the fourth base from the 5' end. The designed nucleic acid probe 1 was BODIPY FL-(5')cca (BODIPY 581/591)ttg agg gga tgg ca(3') (SEQ ID NO: 4).

Initially, the phosphate group of cytidylic acid was modified with a linker —$(CH_2)_6$—SH using 5' Amino-Modifier C6 Kit (Glen Research Corp., USA). The OH group on the carbon atom at the 6-position of the base ring of thymine was modified with a linker —$(CH_2)_7$—$NH_2$ using Amino-Modifier C2dT Kit (Glen Research Corp., USA). Using these modified cytidylic acid and thymidine, an oligonucleotide having the following base sequence was prepared synthetically using a DNA synthesizer (ABI 394; PerkinElmer Japan Co., Ltd.). The prepared oligonucleotide was a deoxyribooligonucleotide having a base sequence: $HS(CH_2)_6$-(5')cca ($H_2N$—$(CH_2)_7$-)ttg agg gga tgg ca(3') (SEQ ID NO: 4), in which the phosphate group at the 5' end was modified with the linker —$(CH_2)_6$—SH, and the OH group on the carbon atom at the 6-position of the base ring of thymine, the fourth base from the 5' end, was modified with the linker —$(CH_2)_7$—$NH_2$. The DNA was synthetically prepared according to a beta-cyanoethylphosphoramidite (2-cyanoethylphosphoramidite) method with 5' end Tr ON. After preparation, the protecting group was deprotected by a treatment with 28% aqueous ammonia at 55° C. for 5 hours.

Purification of Prepared Product:

The above-prepared synthetic oligonucleotide-containing solution was concentrated to dryness. The dried residues were dissolved in 0.5 M $NaHCO_3$/$Na_2CO_3$ buffer (pH 9.0). The resultant solution was subjected to a gel filtration method using an NAP-10 column (a product of Pharmacia Co.) to thereby remove unreacted materials.

Labeling with Acceptor Dye:

The filtrated product was dried to dryness and the dried residues were then dissolved in 150 μL of sterile water (oligonucleotide A solution). A total of 1 mg of BODIPY 581/591-NHS (Molecular Probes Inc., USA) was dissolved in 100 μL of dimethylformamide (DMF) and the solution containing BODIPY 581/591 NHS was subjected to addition of the oligonucleotide A solution (150 μL) and 150 μL of 1 M $NaHCO_3$/$Na_2CO_3$ buffer and mixing after the addition, followed by mixing by stirring at room temperature vernight.

Purification of Prepared Product:

The resultant mixture was subjected to a gel filtration method by using an NAP-25 (a product of Pharmacia Co.) to remove unreacted materials. Next, the protective group was deprotected with 2% TFA. The resultant was subjected to a reversed phase HPLC method using a SEP-PAC $C_{18}$ column to obtain a fraction containing a target product comprising the targeted oligonucleotide with the acceptor dye BODIPY 581/591 bound to the linker —$(CH_2)_7$—$NH_2$ of the oligonucleotide. The obtained fraction was subjected to a gel filtration method using a NAP-10 (a product of Pharmacia Co.).

Labeling with Donor Dye:

The gel-filtrated product-containing fraction was concentrated to dryness and the dried residue was dissolved in 150 μL of sterile water (oligonucleotide B solution). A total of 1 mg of BODIPY FL-Chloride (Molecular Probes Inc., USA) was dissolved in 100 μL of DMF and the resultant solution was then subjected to addition of the oligonucleotide B solution and 150 μL of 1 M $NaHCO_3$/$Na_2CO_3$ buffer, followed by overnight reaction at room temperature after stirring. Thereby the oligonucleotide with the donor dye BODIPY FL bound to the linker —$(CH_2)_6$—SH at the 5' end was prepared.

Purification of Prepared Product:

The above reacted product was subjected to a gel filtration method using a NAP-25 (Pharmacia Co.) to remove unreacted materials, and the obtained filtrated product was then subjected to a reversed phase HPLC method in the same manner as above and thereby yielded nucleic acid probe 1 labeled with a donor dye and acceptor dye according to the present invention. Nucleic acid probe 1 was an oligonucleotide labeled with the acceptor dye BODIPY 581/591 at the thymine base, the fourth base from the 5' end, and with the donor dye BODIPY FL at the phosphate group at the 5' end. Incidentally, the nucleic acid probe of the present invention was eluted after the elution of the oligpnucleotide labeled with the acceptor dye alone.

The amount of the nucleic acid probe of the present invention was determined at 260 nm using a spectrophotometer. The wavelengths of the spectrophotometer was scanned at 650 to 220 nm for the absorptivity that showed absorption of BODIPY FL, BODIPY 581/591, and a DNA. The purity of the purified finnal product was assayed by reversed phase HPLC in the same manner as above; the purified product showed a single peak.

The condition of the reversed phase chromatography was as follows:

Elution solvent A: 0.05 N TEAA 5% $CH_3CN$

Elution solvent B: (for gradient): 0.05 N TEAA 40% $CH_3CN$

Column: SEP-PAK C18; 6×250 mm

Elution rate: 1.0 ml/min

Temperature: 40° C.

Detection: 254 nm

Example 2

Preparation of Probe Labeled with Acceptor Dye BODIPY 581/591 alone ((5')cca (BODIPY 581/591)ttg agg gga tgg ca(3')) (Nucleic Acid Probe 2: SEO ID NO: 4):

Nucleic acid probe 2 was prepared by the same method as that of nucleic acid probe 1, except for the procedures for binding the donor dye BODIPY FL to the phosphate group at the 5' end.

Example 3

Preparation of Probe Labeled with Donor Dye BODIPY FL alone ((BODIPY FL-(5')cca ttg agg gga tgg ca(3')) (Nucleic Acid Probe 3; SEQ ID NO: 4):

A nucleic acid probe was prepared by the same method as that of nucleic acid probe 1, except for the procedures for binding the acceptor dye BODIPY 581/591 to the phosphate group at the 5' end.

Example 4

Preparation of Target Nucleic Acid:

An oligonucleotide having a base sequence of (5')tgc cat ccc ctc aat gg(3') (SEQ ID NO: 3) was prepared in the same manner as tha in the preparation of the aforementioned oligonucleotide and thereby yielded a target nucleic acid for use in the present invention.

Example 5

Fluorescence Intensity Determination of Reaction System in which Target Nucleic Acid was Hybridized with Probe of the Present Invention:

In a quartz cell (10 mm×10 mm in size; capacity: 4 mL) was placed 500 μL of a buffer [120 mM NaCl (final concentration: 30 mM), 120 mM Tris-HCl (final concentration: 30 mM; pH=7.2)], followed by addition of 1460 μL of sterile distilled water and then stirring. To the mixture was added 8.0 μL of a 10 μM solution of nucleic acid probe 1 of the present invention or a solution of nucleic acid probe 2 (final concentration of the nucleic acid probe: 40 nM), followed by stirring. The mixture was held at 30° C. and fluorescence intensities thereof were examined at an excitation wavelength of 490 nm (8 nm wide) and a measuring fluorescence wavelength of 580 nm (8 nm wide). The reaction system was then controlled at 60° C. and was subjected to addition of 32.0 μL of a 10 μM solution of the target nucleic acid (final concentration of the target nucleic acid: 160 nM) and then stirring. Further, the fluorescence entinsities thereof were examined. The reaction system was kept at 30° C. to thereby allow the nucleic acid probe to hybridize with the target nucleic acid, and the fluorescence intensities were examined. The results are shown in Tables 1 and 2.

In these procedures, the temperature of a cell (reaction temperature) was controlled using a thermostatic cell holder, a low-temperature circulation apparatus with a program system for crystallization PCC-7000 (a product of Tokyo Rika Kikai Co., Ltd.). The fluorescence intensity was measured using a fluorophotometer LS 50B (a product of PerkinElmer Inc.).

TABLE 1

Changes in Fluorescence Intensity at 580 nm Before and After Hybridization (HYB) (excited at 490 nm)

| Test System | Before HYB (60° C.) | After HYB (30° C.) | Decrease in Fluorescence Intensity | Decrease Percentage (%) |
| --- | --- | --- | --- | --- |
| Nucleic acid probe 1 and target nucleic acid | 24.82 | 4.10 | 20.72 | 83.5 |
| Nucleic acid probe 2 and target nucleic acid | 0.51 | 0.55 | −0.04 | −107.8 |

HYB: Hybridization
Decrease in Fluorescence Intensity (Differential Decrease in Fluorescence Intensity Between Before Hybridization and After Hybridization): [Fluorescence intensity before hybridization] - [Fluorescence intensity after hybridization]
Decrease Percentage: [Decrease in fluorescence intensity]/[Fluorescence intensity before hybridization]

TABLE 2

Changes in Fluorescence Intensity at 510 nm Before and After Hybridization (HYB) (excited at 490 nm)

| Test System | Before HYB (60° C.) | After HYB (30° C.) | Decrease in Fluorescence Intensity | Decrease Percentage (%) |
| --- | --- | --- | --- | --- |
| Nucleic acid probe 1 and target nucleic acid | 10.5 | 7.8 | 2.7 | 25.71 |
| Nucleic acid probe 3 and target nucleic acid | 55.56 | 9.6 | 45.96 | 82.72 |

HYB: Hybridization
Decrease in Fluorescence Intensity Differential Decrease in Fluorescence Intensity Between Before Hybridization and After Hybridization): [Fluorescence intensity before hybridization] - [Fluorescence intensity after hybridization]
Decrease Percentage: [Decrease in fluorescence intensity]/[Fluorescence intensity before hybridization]

Table 1 shows the fluorescence intensity of the acceptor dye BODIPY 581/591, and Table 2 shows the fluorescence intensity of the donor dye.

Table 1 indicates the followings:

The fluorescence intensity of the acceptor dye before hybridization in the test system containing nucleic acid probe 1 and the target nucleic acid is much higher than that in the test system containing nucleic acid probe 2 and the target nucleic acid. This is capable of being explained by the phenomena that FRET occurs between the donor dye BODIPY FL and the acceptor dye BODIPY 581/591 to thereby allow the acceptor dye to emit fluorescence in nucleic acid probe 1. In contrast, FRET does not occur and fluorescence is not emitted in nucleic acid probe 2, since it has no donor dye in its molecule.

After hybridization, the fluorescence intensity significantly decreases in the test system containing nucleic acid probe 1 and the target nucleic acid. In contrast, the fluorescence intensity changes little in the test system containing nucleic acid probe 2 and the target nucleic acid. This is capable of being explained by the phenomena that nucleic acid probe 1 hybridizes with the target nucleic acid and the hybridization causes the donor dye to approach the G-C hydrogen bond complex; the energy of the donor dye transfers to the G-C hydrogen bond complex.

Table 2 indicates the followings:

The fluorescence intensity of the donor dye before hybridization in the test system containing nucleic acid probe 1 and the target nucleic acid is much higher than that in the test system containing nucleic acid probe 2 and the target nucleic acid shown in Table 1. This is capable of being explained by the phenomena that FRET occurs between the donor dye BODIPY FL and the acceptor dye BODIPY 581/591, and the energy of the donor dye transfers to the acceptor dye in nucleic acid probe 1. In contrast, the nucleic acid probe 3 shown in Table 2 has no acceptor dye in its molecule, thereby does not induce FRET and emits fluorescence.

After hybridization, the fluorescence intensity in the test system containing nucleic acid probe 1 and the target nucleic acid decreases little. This is capable of being explained by the phenomena that the donor dye approaches the G-C hydrogen bond complex upon hybridization with the target nucleic acid, and the energy transfers to the G-C hydrogen bond complex rather than to the acceptor dye. The fluorescence intensity in the test system containing nucleic acid probe 3 and the target nucleic acid markedly decreases. This is capable of being explained by the phenomena that the donor dye approaches the G-C hydrogen bond complex upon hybridization with the target nucleic acid, and the energy which has been consumed to emit fluorescence now transfers to the G-C hydrogen bond complex.

Tables 1 and 2 show that the nucleic acid probe of the present invention is designed so as to decrease the fluorescence intensities of both the donor dye and acceptor dye upon hybridization with the target nucleic acid.

Example 6

An oligodeoxyribonucleotide having a base sequence of (5')aacgatgcca tggatttgg(3') (SEQ ID NO: 5) as a target nucleic acid B was prepared in the same manner as in Examples 1, 2, 3 and 4.

Nucleic acid probe 4 according to the present invention that can hybridize with the target nucleic acid B was prepared in the same manner as in the aforementioned examples by labeling an oligonucleotide with X-rhodamine as an acceptor dye and with BODIPY FL as a donor dye. Nucleic acid probe 4 had the following structure: BODIPY FL-(5')ccaaat(X-Rhodamine)ccat ggcatca tt(3') (SEQ ID NO: 6).

Fluorescence Intensity Determination in Reaction System Containing Nucleic Acid Probe 1 of the Invention Hybridized with Target Nucleic Acid A and Nucleic Acid Probe 4 of the Invention Hybridized with Target Nucleic Acid B:

In a quartz cell (10 mm×10 mm in size; capacity: 4 mL) was placed 500 µL of a buffer [120 mM NaCl (final concentration: 30 mM), 120 mM Tris-HCl (final concentration: 30 mM; pH=7.2)], followed by addition of 1460 µL of sterile distilled water and then stirring. To the mixture was added 8.0 µL of a 10 µM solution of nucleic acid probes 1 and 4 of the present invention (final concentration of the nucleic acid probes: 40 nM), and followed by stirring. The mixture was held at 45° C. and the fluorescence intensities were determined at 580 nm (5 nm wide) on the probe 1 and at 610 nm (5 nm wide) on the probe 4 both at an excitation wavelength of 490 nm (8 nm wide). Next, 32.0 µL each of solutions of the target nucleic acids A and B at individual concentrations indicated in Table 3 were added to the mixture and was stirred. The fluorescence intensities of the resultant mixtures were determined, and the results are shown in Table 3.

The same thermostatic cell holder, fluorophotometer, and other apparatus and procedures as in the above examples were employed herein.

TABLE 3

Changes in Fluorescence Intensity at 580 nm and 610 nm Before and After Hybridization (HYB) (both excited at 490 nm)

| Test System | Target Nucleic Acid Concentration (µM) | Before HYB (45° C.) | After HYB (45° C.) | Decrease in Fluorescence Intensity | Decrease Percentage (%) |
|---|---|---|---|---|---|
| 580 nm | 0 | 110 | 108 | 2 | 1.8 |
| (Target | 20 | 107 | 67 | 40 | 37.4 |
| Nucleic | 40 | 101 | 30 | 71 | 70.2 |
| Acid A) | 60 | 98 | 22 | 76 | 77.7 |
| 610 nm | 0 | 80 | 85 | 5 | 0.6 |
| (Target | 20 | 75 | 50 | 25 | 33.3 |
| Nucleic | 40 | 80 | 28 | 52 | 65.0 |
| Acid B) | 60 | 76 | 18 | 58 | 76.3 |

HYB: Hybridization
Decrease in Fluorescence Intensity (Differential Decrease in Fluorescence Intensity Between Before Hybridization and After Hybridization): [Fluorescence intensity before hybridization] − [Fluorescence intensity after hybridization]
Decrease Percentage: [Decrease in fluorescence intensity]/[Fluorescence intensity before hybridization]

Table 3 shows that the fluorescence intensities at 580 nm and 610 nm decreases after hybridization to a degree depending on the concentration of the target nucleic acid. When excited at 490 nm, changes in the fluorescence intensity at 580 nm belongs to those of the probe 1 of the present invention, and those at 610 nm belongs to those of the probe 4 of the invention. These results show that, by using the nucleic acid determination method and the nucleic acid probes of the present invention, plural types of target nucleic acids can be easily determined in parallel even if the plural target nucleic acids are contained in one assay system.

INDUSTRIAL APPLICABILITY

The nucleic acid probes of the present invention have the above configuration, show markedly decreased fluorescence intensities of both the donor dye and acceptor dye after hybridization with the target nucleic acids and thereby enable easy determination of the target nucleic acids even in trace amounts precisely in a short time.

Donor dyes must transfer their energy to a G-C hydrogen bond complex and are limited in their types. However, acceptor dyes do not require such a property, and any acceptor dyes can be used herein as long as they are capable of receiving transferred energy. Accordingly, different nucleic acid probes emitting fluorescence in different colors (having different fluorescence wavelengths) can be prepared using one donor dye (i.e., at one excitation wavelength) according to the present invention. This configuration simplifies the optical system for excitation in a nucleic acid analyzer for determining multiple types of nucleic acids, since the device (analyzer) is usable only by having one excitation laser. In other words, the invention can simplify the design and preparation of such a nucleic acid analyzer.

In addition, in even a simple nucleic acid analyzer having an excitation laser at one wavelength, multiple types of nucleic acid probes can be utilized; thereby multiple types of target nucleic acids can be in parallel determined using one analyzer.

The invention claimed is:

1. A nucleic acid probe for determining one or more types of target nucleic acids, comprising a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising a fluorescent dye (a donor dye) capable of serving as a donor dye and a fluorescent dye (an acceptor dye) capable of serving as an acceptor dye, wherein said acceptor dye is BODIPY 581/591 or x-rhodamine, with the proviso that:

when the acceptor dye is BODIPY 581/591, the donor dye is one fluorescent dye selected from the group consisting of BODIPY FL, BODIPY 493/503, 5-FAM, Tetramethylrhodamine, and 6-TAMRA, or a combination thereof, and when the acceptor dye is x-rhodamine, the donor dye is one fluorescent dye selected from the group consisting of BODIPY FL, BODIPY 493/503, Tetramethylrhodamine, and 6-TAMRA, or a combination thereof wherein the nucleic acid probe has a base sequence and is labeled with the fluorescent dyes such that the fluorescence intensity of the donor dye and the acceptor dye decrease upon hybridization with a target nucleic acid, wherein said nucleic acid probe is labeled with a donor dye at a 5'- or 3'-end containing cytosine and said nucleic acid probe is labeled with an acceptor dye such that the distance between the bases labeled with the donor dye and the acceptor dye is from 0 to 35 bases, and wherein the site of the end labeling is one group selected from the group consisting of the 3'-hydroxyl of ribose or deoxyribose of the 3'-end containing cytosine, the 5'-hydroxyl of ribose or deoxyribose of the 5'-end containing cytosine, and the 5'phosphate group of the 5'-end containing cytosine.

2. The nucleic acid probe for determining one or more types of target nucleic acids according to claim 1, wherein said nucleic acid probe is labeled with the donor dye in said end and has a base sequence designed such that, when said nucleic acid probe hybridizes with the target nucleic acid at the end region, the target nucleic acid has at least one G (guanine) in its base sequence as a first to third base from its terminal base hybridized with the end base of the nucleic acid probe.

3. A method for nucleic acid determination, the method comprising, in this order:

adding one or more types of the nucleic acid probes into an assay system containing one or more types of target nucleic acids, wherein said nucleic acid probes are labeled with acceptor dyes emitting fluorescence in different colors from each other;

measuring the fluorescence intensity caused by the acceptor dyes in an assaying system at wavelengths specific to the colors of the fluorescence from the acceptor dyes;

hybridizing said nucleic acid probes to said target nucleic acid(s);

measuring the fluorescence intensity in the assaying system at the same wavelengths as prior to hybridization; and determining the differential decrease(s) in fluorescence intensity by comparing the profile before said hybridizing and after said hybridizing wherein said one or more types of the nucleic acid probes are nucleic acid probes for determining one or more types of target nucleic acids, comprising:

a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising:

(a) a fluorescent dye (a donor dye) capable of serving as a donor dye:

(i) being excited at a specific wavelength and emitting light at a specific wavelength, (ii) being capable of transferring its light-emitting energy to a dye capable of serving as an acceptor dye, and (iii) being capable of transferring its light emitting energy to a G-C base pair complex in its base sequence as a first to third base from the base labeled with the fluorescent dye (the donor dye); and (b) a fluorescent dye (an acceptor dye) capable of serving as an acceptor dye, wherein the nucleic acid probe has a base sequence and is labeled with the fluorescent dyes such that the fluorescence intensity of the donor dye and the acceptor dye decrease upon hybridization with a target nucleic acid; and wherein the nucleic acid probe:

(1) is labeled with the donor dye in an end; and (2) has a base sequence designed such that, when the nucleic acid probe hybridizes with the target nucleic acid at the end, the target nucleic acid has at least one G (guanine) in its base sequence as a first to third base from its base hybridized with the terminal base of the probe.

4. A method for analyzing or determining at least one member selected from the group consisting of polymorphism and mutation of one or more types of target nucleic acids in an assay system, which comprises, in this order:

adding one or more types of the nucleic acid probes into an assay system containing one or more types of target nucleic acids wherein said nucleic acid probes are labeled with acceptor dyes emitting fluorescence in different colors from each other;

measuring the fluorescence intensity caused by the acceptor dyes in an assaying system at wavelengths specific to the colors of the fluorescence from the acceptor dyes;

hybridizing said nucleic acid probes to said target nucleic acid(s);

measuring the fluorescence intensity in the assaying system at the same wavelengths as prior to hybridization; and determining the differential decrease(s) in fluorescence intensity by comparing the profile before said hybridizing and after said hybridizing wherein said one or more types of the nucleic acid probes are nucleic acid probes for determining one or more types of target nucleic acids, comprising:

a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising:

(a) a fluorescent dye (a donor dye) capable of serving as a donor dye:
(i) being excited at a specific wavelength and emitting light at a specific wavelength,
(ii) being capable of transferring its light-emitting energy to a dye capable of serving as an acceptor dye, and
(iii) being capable of transferring its light emitting energy to a G-C base pair complex in the vicinity of the fluorescent dye (the donor dye); and (b) a fluorescent dye (an acceptor dye) capable of serving as an acceptor dye, wherein the nucleic acid probe has a base sequence and is labeled with the fluorescent dyes such that the fluorescence intensity of the donor dye and the acceptor dye decrease upon hybridization with a target nucleic acid;

and wherein the nucleic acid probe:
(1) is labeled with the donor dye in an end; and
(2) has a base sequence designed such that, when the nucleic acid probe hybridizes with the target nucleic acid at the end, the target nucleic acid has at least one G (guanine) in its base sequence as a first to third base from its base hybridized with the terminal base of the probe.

5. The method according to claim 3, wherein the fluorescent dye capable of serving as a donor dye is selected from BODIPY FL, BODIPY 493/503, 5-FAM, Tetramethylrhodamine, and 6-TAMRA.

6. The method according to claim 3, wherein the nucleic acid probe is labeled with the donor dye in an end and the acceptor dye such that the distance between the bases labeled with the donor dye and the acceptor dye ranges from 0 to 35 bases.

7. The method according to claim 3, wherein the nucleic acid probe has a C base at the 5'- or 3'- end and is labeled with the donor dye at the 5'- or 3'- end.

8. The method according to claim 3, wherein the nucleic acid probe is labeled with the donor dye at one member selected from the group consisting of a C (cytosine), a phosphate group and an OH group of the ribose or deoxyribose moiety of an end containing C (cytosine).

9. The method according to claim 4, wherein the fluorescent dye capable of serving as a donor dye is selected from BODIPY FL, BODIPY 493/503, 5-FAM, Tetramethylrhodamine, and 6-TAMRA.

10. The method according to claim 4, wherein the nucleic acid probe is labeled with the donor dye in an end and the acceptor dye such that the distance between the bases labeled with the donor dye and the acceptor dye ranges from 0 to 35 bases.

11. The method according to claim 4, wherein the nucleic acid probe has a C base at the 5'- or 3'- end and is labeled with the donor dye at the 5'- or 3'- end.

12. The method according to claim 4, wherein the nucleic acid probe is labeled with the donor dye at one member selected from the group consisting of a C (cytosine), a phosphate group and an OH group of the ribose or deoxyribose moiety of an end containing C (cytosine).

13. The method according to claim 3, wherein said nucleic acid probes are in a quantitative excess as compared to the target nucleic acid(s).

14. The method according to claim 4, wherein said nucleic acid probes are in a quantitative excess as compared to the target nucleic acid(s).

15. A nucleic acid probe for determining one or more types of target nucleic acids, comprising a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising a fluorescent dye (a donor dye) capable of serving as a donor dye and a fluorescent dye (an acceptor dye) capable of serving as an acceptor dye, wherein said donor dye is one fluorescent dye selected from the group consisting of BODIPY FL, BODIPY 493/503, 5-FAM, Tetramethylrhodamine, and 6-TAMRA, or a combination thereof, wherein the nucleic acid probe has a base sequence and is labeled with the fluorescent dyes such that the fluorescence intensity of the donor dye and the acceptor dye decrease upon hybridization with a target nucleic acid, wherein said nucleic acid probe is labeled with a donor dye at a 5'- or 3'-end containing cytosine and said nucleic acid probe is labeled with an acceptor dye such that the distance between the bases labeled with the donor dye and the acceptor dye is from 0 to 35 bases, wherein the site of the end labeling is one group selected from the group consisting of the 3'-hydroxyl of ribose or deoxyribose of the 3'-end containing cytosine, the 5'-hydroxyl of ribose or deoxyribose of the 5'-end containing cytosine, and the 5'phosphate group of the 5'-end cytosine, and wherein the structure of said nucleic acid probe in the end region to be labeled is either CC or CCC.

16. The nucleic acid probe for determining one or more types of target nucleic acids according to claim 15, wherein the nucleic acid probe is labeled with the donor dye in an end and has a base sequence designed such that, when the probe hybridizes with the target nucleic acid at the end, the target nucleic acid has at least one G (guanine) in its base sequence as a first to third base from its base hybridized with the end base of the nucleic acid probe.

17. The nucleic acid probe for determining one or more types of target nucleic acids according to claim 15, wherein the nucleic acid probe is labeled with the donor dye in an end and the acceptor dye such that the distance between the bases labeled with the donor dye and the acceptor dye ranges from 0 to 10 bases.

18. A nucleic acid probe for determining one or more types of target nucleic acids, comprising a single-stranded nucleic acid being labeled with plural fluorescent dyes, the fluorescent dyes comprising at least one pair of fluorescent dyes to induce fluorescence resonance energy transfer (FRET), the pair of fluorescent dyes comprising a fluorescent dye (a donor dye) capable of serving as a donor dye and a fluorescent dye (an acceptor dye) capable of serving as an acceptor dye, wherein said donor dye is selected from the group consisting of BODIPY FL, BODIPY 493/503, Tetramethylrhodamine, and 6-TAMRA, or a combination thereof, wherein the nucleic acid probe has a base sequence and is labeled with the fluorescent dyes such that the fluorescence intensity of the donor dye and the acceptor dye decrease upon hybridization with a target nucleic acid, wherein said nucleic acid probe is labeled with a donor dye at a 5'- or 3'-end containing cytosine and said nucleic acid probe is labeled with an acceptor dye such that the distance between the bases labeled with the donor dye and the acceptor dye is from 0 to 35 bases, wherein the site of the end labeling is one group selected from the group consisting of the 3'-hydroxyl of ribose or deoxyribose of the 3'-end containing cytosine, the 5'-hydroxyl of ribose or deoxyribose of the 5'-end containing cytosine, and the 5' phosphate group of the 5'-end containing cytosine.

19. The nucleic acid probe for determining one or more types of target nucleic acids according to claim 18, wherein the nucleic acid probe is labeled with the donor dye in an end and has a base sequence designed such that, when the probe hybridizes with the target nucleic acid at the end, the target nucleic acid has at least one G (guanine) in its base sequence as a first to third base from its base hybridized with the end base of the nucleic acid probe.

20. The nucleic acid probe for determining one or more types of target nucleic acids according to claim 18, wherein the nucleic acid probe is labeled with the donor dye in an end and the acceptor dye such that the distance between the bases labeled with the donor dye and the acceptor dye ranges from 0 to 10 bases.

21. A method for nucleic acid determination according to claim 3, wherein said one or more types of nucleic acid probes are one or more nucleic acid probes according to claim 1.

22. A method for analyzing or determining at least one member selected from the group consisting of polymorphism and mutation of one or more types of target nucleic acids in an assay system according to claim 4, wherein said one or more types of nucleic acid probes are one or more nucleic acid probes according to claim 1.

23. A method for nucleic acid determination according to claim 3, wherein said one or more types of nucleic acid probes are one or more nucleic acid probes according to claim 15.

24. A method for analyzing or determining at least one member selected from the group consisting of polymorphism and mutation of one or more types of target nucleic acids in an assay system according to claim 4, wherein said one or more types of nucleic acid probes are one or more nucleic acid probes according to claim 15.

25. A method for nucleic acid determination according to claim 3, wherein said one or more types of nucleic acid probes are one or more nucleic acid probes according to claim 18.

26. A method for analyzing or determining at least one member selected from the group consisting of polymorphism and mutation of one or more types of target nucleic acids in an assay system according to claim 4, wherein said one or more types of nucleic acid probes are one or more nucleic acid probes according to claim 18.

* * * * *

UNITED STATES PATENT AND TRADEMARK OFFICE
CERTIFICATE OF CORRECTION

PATENT NO.       : 7,273,700 B2  
APPLICATION NO.  : 10/399407  
DATED            : September 25, 2007  
INVENTOR(S)      : Kurane et al.

It is certified that error appears in the above-identified patent and that said Letters Patent is hereby corrected as shown below:

On the title page, Item (75), the inventor information is incorrect. Item (75) should read:

-- (75) Inventors:  Ryuichiro Kurane, Tsukuba (JP);  
Takahiro Kanagawa, Tsukuba, (JP);  
Yoichi Kamagata, Tsukuba (JP);  
Masaki Torimura, Tsukuba (JP);  
Shinya Kurata, Tokyo, (JP); Kazutaka Yamada, Tokyo (JP); Toyokazu Yokomaku, Tokyo (JP) --

Signed and Sealed this

Fourth Day of December, 2007

JON W. DUDAS  
*Director of the United States Patent and Trademark Office*

SEQUENCE LISTING

<160> NUMBER OF SEQ ID NOS: 6

<210> SEQ ID NO 1
<211> LENGTH: 21

```
<212> TYPE: DNA
<213> ORGANISM: Artificial Sequence
<220> FEATURE:
<223> OTHER INFORMATION: Synthetic DNA

<400> SEQUENCE: 1
tcctttgagt tcccggccgg a                                              21

<210> SEQ ID NO 2
<211> LENGTH: 32
<212> TYPE: DNA
<213> ORGANISM: Artificial Sequence
<220> FEATURE:
<223> OTHER INFORMATION: Synthetic DNA

<400> SEQUENCE: 2
ccctggtcgt aagggccatg atgacttgac gt                                  32

<210> SEQ ID NO 3
<211> LENGTH: 17
<212> TYPE: DNA
<213> ORGANISM: Artificial Sequence
<220> FEATURE:
<223> OTHER INFORMATION: Synthetic DNA

<400> SEQUENCE: 3
tgccatcccc tcaatgg                                                   17

<210> SEQ ID NO 4
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: modified_base
<222> LOCATION: (1)..(1)
<223> OTHER INFORMATION: BODIPY FL or HS-(CH2)6-
<220> FEATURE:
<221> NAME/KEY: modified_base
<222> LOCATION: (4)..(4)
<223> OTHER INFORMATION: BODIPY 581/591 or H2N-(CH2)7-

<400> SEQUENCE: 4
ccattgaggg gatggca                                                   17

<210> SEQ ID NO 5
<211> LENGTH: 19
<212> TYPE: DNA
<213> ORGANISM: Artificial Sequence
<220> FEATURE:
<223> OTHER INFORMATION: Synthetic DNA

<400> SEQUENCE: 5
aacgatgcca tggatttgg                                                 19

<210> SEQ ID NO 6
<211> LENGTH: 19
<212> TYPE: DNA
<213> ORGANISM: Artificial Sequence
<220> FEATURE:
<223> OTHER INFORMATION: Synthetic DNA
<220> FEATURE:
<221> NAME/KEY: modified_base
<222> LOCATION: (1)..(1)
<223> OTHER INFORMATION: BODIPY FL
<220> FEATURE:
<221> NAME/KEY: modified_base
<222> LOCATION: (7)..(7)
```

-continued

<223> OTHER INFORMATION: X-Rhodamine

<400> SEQUENCE: 6
ccaaatccat ggcatcatt                                                    19